United States Patent
Ben-Yishai

(10) Patent No.: US 11,931,292 B2
(45) Date of Patent: Mar. 19, 2024

(54) SYSTEM AND METHOD FOR IMPROVED ELECTRONIC ASSISTED MEDICAL PROCEDURES

(71) Applicant: BEYEONICS SURGICAL LTD., Haifa (IL)

(72) Inventor: Rani Ben-Yishai, Haifa (IL)

(73) Assignee: BEYEONICS SURGICAL LTD., Haifa (IL)

( * ) Notice: Subject to any disclaimer, the term of this patent is extended or adjusted under 35 U.S.C. 154(b) by 0 days.

(21) Appl. No.: 17/870,297

(22) Filed: Jul. 21, 2022

(65) Prior Publication Data

US 2022/0354691 A1 Nov. 10, 2022

Related U.S. Application Data

(63) Continuation of application No. PCT/IL2021/050069, filed on Jan. 22, 2021.

(60) Provisional application No. 62/964,456, filed on Jan. 22, 2020.

(51) Int. Cl.
*A61F 9/007* (2006.01)
*A61B 3/00* (2006.01)
*A61B 3/10* (2006.01)
*A61F 9/008* (2006.01)

(52) U.S. Cl.
CPC ............ *A61F 9/007* (2013.01); *A61B 3/0025* (2013.01); *A61B 3/102* (2013.01); *A61F 2009/00872* (2013.01)

(58) Field of Classification Search
CPC ...... A61F 9/007; A61F 9/00736; A61F 9/008; A61F 9/00812; A61F 9/00825; A61F 9/00834; A61F 2009/00851; A61F 2009/00865; A61F 2009/0087; A61F 2009/00872; A61F 2009/00874; A61F 2009/00889; A61B 3/10; A61B 3/102
USPC .......................................... 606/4–6; 128/898
See application file for complete search history.

(56) References Cited

U.S. PATENT DOCUMENTS

| | | | | |
|---|---|---|---|---|
| 7,831,294 | B2 * | 11/2010 | Viswanathan | A61B 34/20 600/424 |
| 8,554,307 | B2 * | 10/2013 | Razzaque | A61B 8/483 600/407 |
| 10,517,690 | B2 | 12/2019 | Kosmecki et al. | |
| 11,484,363 | B2 * | 11/2022 | Schneider | A61B 34/20 |

(Continued)

FOREIGN PATENT DOCUMENTS

| | | | | |
|---|---|---|---|---|
| WO | WO-2021149056 A1 * | 7/2021 | | A61B 3/0025 |
| WO | WO-2022249190 A1 * | 12/2022 | | |

OTHER PUBLICATIONS

International Search Report and Written Opinion for PCT Application No. PCT/IL2021/050069, dated Jun. 3, 2021.

(Continued)

*Primary Examiner* — Ahmed M Farah
(74) *Attorney, Agent, or Firm* — PEARL COHEN ZEDEK LATZER BARATZ LLP

(57) ABSTRACT

Methods and systems for displaying an overlay superimposed with an intraoperative image of surgical field in a medical ophthalmic procedure, such that the overlay appears at a desired depth within the image are provided. Methods and system for displaying an overlay superimposed with a stereoscopic intraoperative image pair of a surgical field in a medical ophthalmic procedure are provided.

14 Claims, 9 Drawing Sheets

(56) References Cited

U.S. PATENT DOCUMENTS

| | | | |
|---|---|---|---|
| 2007/0238981 A1* | 10/2007 | Zhu | A61B 34/20 600/424 |
| 2010/0177163 A1* | 7/2010 | Yang | G06T 19/006 348/E13.001 |
| 2011/0050852 A1* | 3/2011 | Lamprecht | A61B 34/37 348/45 |
| 2011/0105898 A1* | 5/2011 | Guthart | A61B 1/04 600/109 |
| 2012/0226150 A1* | 9/2012 | Balicki | A61B 3/102 600/424 |
| 2015/0077528 A1 | 3/2015 | Awdeh | |
| 2018/0309980 A1 | 10/2018 | Ootsuki | |
| 2018/0322666 A1 | 11/2018 | Tripathi et al. | |
| 2019/0000314 A1 | 1/2019 | Awdeh | |
| 2019/0117459 A1 | 4/2019 | Berlin | |
| 2023/0071841 A1* | 3/2023 | Ben-Yishai | A61B 90/37 |

OTHER PUBLICATIONS

Extended European Search Report for EP Patent Application No. 21743627.8, dated May 15, 2023.

* cited by examiner

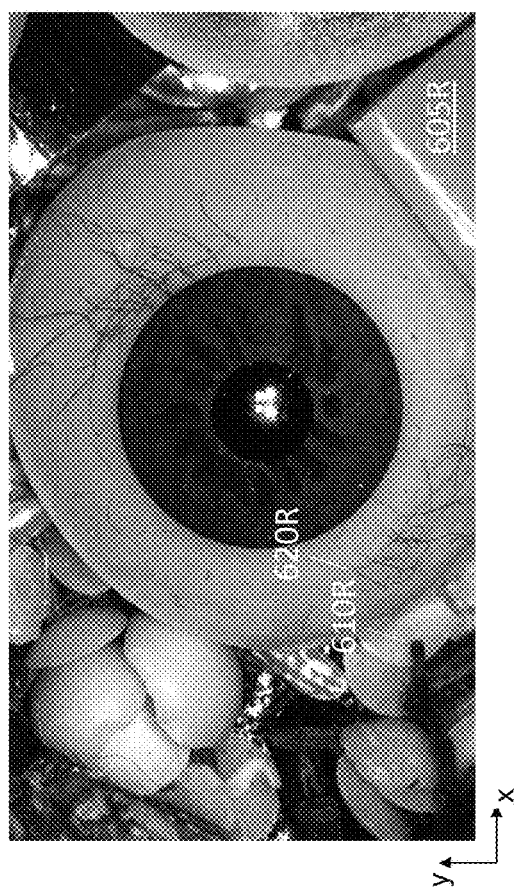
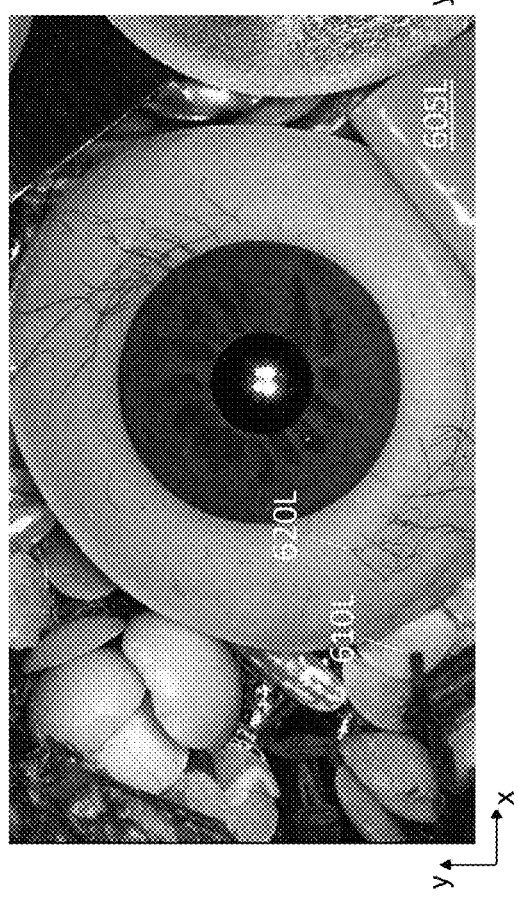
FIG. 6B
FIG. 6A

SYSTEM AND METHOD FOR IMPROVED ELECTRONIC ASSISTED MEDICAL PROCEDURES

CROSS REFERENCE TO RELATED APPLICATIONS

This application is a continuation of International Patent Application No. PCT/IL2021/050069, filed on Jan. 22, 2021, which claims the benefit of U.S. Provisional Patent Application No. 62/964,456 filed on Jan. 22, 2020, both of which are incorporated herein by reference in their entirety.

FIELD OF THE INVENTION

The invention relates generally to the field of computer assisted surgeries. In particular, the invention relates to image guided surgeries.

BACKGROUND OF THE INVENTION

Currently, computing systems for assisted surgeries exist (e.g., image guided surgical systems). Some current systems include displays that can allow persons (e.g., medical professionals, surgeons, nurses, and/or other persons) to view medical data while a medical procedure (e.g., a surgery) is performed. In some systems, a desired location for an object with respect to the surgery can be displayed to a surgeon. In some systems, an object image can be superimposed on (e.g., overlaid with) an intraoperative image. For example, during intraocular lens (IOL) placement.

In the case of IOL placement, some types of IOLs can require that the IOL is positioned in a specific orientation and/or location within a patient's eye (e.g., toric IOLs, multifocal IOLs). In current systems, a desired orientation and/or location for the IOL with respect to a preoperative image of an eye (e.g., an image of an eye taken prior to the surgery) can be determined by, for example, various current diagnostic devices. The preoperative image can be captured by the diagnostic device concurrently with sampling the data that is used for calculating the desired IOL positioning (orientation and/or location).

When performing computer assisting surgeries, depth perception can be critical for surgeons in various fields of surgery. When overlaying guidance information, it can be desirable to avoid negatively effecting depth perception.

Some current stereoscopic systems (e.g., microscopes) can overlay guidance information in only one of the two optical channels and the overlay can be superimposed in the same manner on all elements in the intraoperative image, regardless of each element's depth in the surgical field. In these systems, the overlay may seem to appear as being at the same depth as the depth of the anatomical region the surgeon is attending and for which the guidance is required, since it appears in focus (as the anatomical region), and at the same time the overlay may seem to appear as being in a completely different depth, since it can occlude anatomical elements and/or tools that may be above the anatomical region. For example, in IOL placement, the overlay may appear above an iris of the eye and above tools that are used to position the IOL. This can cause a surgeon's brain to receive contradicting cues with regard to the overlay depth. This may be extremely uncomfortable for some users, and some of them may choose to close the other eye (e.g., the eye viewing the optical channel without the overlay) while the overlay is displayed.

Currently, when using 2D video (e.g., using standard 2D endoscopes), there can be no stereoscopic vision, and the surgeon can rely on other cues, including occlusion and/or parallax. When using stereoscopic video, such as in microscopes, if a stereoscopic overlay is not at the same depth as the region the surgeon is focused on, it can be uncomfortable to frequently switch attention between the two depths. Additionally, if a stereoscopic overlay is not at the same depth as the region the surgeon is focused on, the overlay may appear as two overlays (e.g., cause double vision).

Therefore, it can be desirable to generate overlay(s) that can appear to a user as being at a desired depth. It can be desirable to generate overlay(s) that avoid occlusion of objects and/or elements in the surgical field that are above the desired depth of the overlay(s). It can be desirable to generate overlay(s) that can provide a user with minimal contradictions within the surgical field. It can be desirable to generate overlay(s) that provide maximal visual comfort and without negatively effecting depth perception.

SUMMARY OF THE INVENTION

In one aspect, the method involves a method for displaying an overlay superimposed with an intraoperative image of a surgical field in a medical ophthalmic procedure. The method includes receiving, by a computing device, the overlay for superimposing with the intraoperative image that is in real-time. The method includes receiving, by a computing device, the intraoperative image of the surgical field in the medical ophthalmic procedure, the surgical field including an element that is to appear as above the overlay, wherein at least one portion of the intraoperative image is associated with the element. The method also includes displaying, by the computing device, the overlay superimposed with the intraoperative image such that an appearance of the overlay in the at least one portion is different than the appearance of the overlay outside of the at least one portion and the overlay appears as below the element and occluded by the element.

In some embodiments, the overlay is determined based on a preoperative image of an eye, a preoperative OCT, an intraoperative image of an eye, an intraoperative OCT, a user input, or any combination thereof. In some embodiments, the overlay includes a guidance overlay for an intraocular lens (IOL) placement, a guidance overlay for a capsulotomy, a guidance overlay for an incision, an enhancement of a membrane or part of a membrane, an enhancement of a capsule or part of a capsule, symbolic overlay, textual overlay, pictorial overlay, or any combination thereof.

In some embodiment, the at least one element comprises: a tool, an iris, a sclera, a corneal reflection, an air bubble, a part of a hand, a lens fragment, or any combination thereof. In some embodiments, the overlay is superimposed such that inside of the at least one portion the overlay is not superimposed and outside of the at least one portion the overlay is superimposed.

In some embodiments, the display overlay appearances in the at least one portion versus outside of the at least one portion differ by at least one of: the overlay transparency, the overlay brightness, the overlay pattern, and the overlay color.

In some embodiments, the method also involves classifying, by the computing device, a pixel of the intraoperative image as being in the at least one portion based on one of the intraoperative image, a previous intraoperative image, or any combination thereof.

In some embodiments, at least one of the intraoperative image, and the previous intraoperative image is segmented, and wherein the classification of a pixel of the intraoperative image as being in the at least one portion is based on the segmentation.

In some embodiments, segments are further classified as one of a: pupil, iris, sclera, tool, corneal reflection, air bubble, part of a hand, lens fragment, IOL, or IOL reflections, and wherein each classified segment is determined to occlude the overlay based on a type of overlay and predefined rules.

In some embodiments, the intraoperative image is one of an intraoperative stereoscopic image pair and the classifying of the pixel is based on the pixel disparity calculated from the stereoscopic image pair. In some embodiments, the classification is based on a gray level value or color value of at least one of the pixel of the intraoperative image, a neighboring pixel, or any combination thereof.

In some embodiments, the method also involves classifying, by the computing device, a pixel of the intraoperative image as being in the at least one portion based on an intraoperative OCT. In some embodiments, data generated by the intraoperative OCT are associated with the pixel of the intraoperative image based on alignment between the intraoperative OCT and a camera that generated the intraoperative image.

In some embodiments, the at least one element is a tool and further comprising, classifying by the computing device, a pixel as being in the at least one portion based at least on a tool tracker. In some embodiments, the classifying is based on a relative position and orientation between the tool and the camera that generated the intraoperative image.

In another aspect, the invention involves a method for displaying an overlay superimposed with a stereoscopic intraoperative image pair of a surgical field in a medical ophthalmic procedure. The method involves receiving, by a computing device, the stereoscopic intraoperative image pair comprising a left intraoperative image and a right intraoperative image of the surgical field in the medical ophthalmic procedure. The method involves receiving, by the computing device, overlay data. The method involves determining, by the computing device, a left-right disparity, wherein the left-right disparity corresponds to a desired depth. The method also involves generating, by the computing device, a left overlay and a right overlay for superimposing with the left and right intraoperative images, based on the overlay data and the left-right disparity, wherein when the left and right intraoperative images are viewed via a stereoscopic display with the left overlay superimposed with the left intraoperative image and the right overlay superimposed with the right intraoperative image, the left overlay and the right overlay appear as a single overlay at the desired depth.

In some embodiments, the overlay data comprises a guidance overlay for an IOL placement, a guidance overlay for a capsulotomy, a guidance overlay for an incision, an enhancement of a membrane or part of a membrane, an enhancement of a capsule or part of a capsule, symbolic overlay, textual overlay, pictorial overlay or any combination thereof.

In some embodiments, determining the left-right disparity is based at least on one of the stereoscopic intraoperative image pair, and a previous stereoscopic intraoperative image pair.

In some embodiments, determining the left-right disparity includes determining, by the computing device, a first location of an element from the surgical field in the left intraoperative image of i) the stereoscopic intraoperative image pair or ii) the previous stereoscopic intraoperative image pair, determining, by the computing device, a second location of the element in the right intraoperative image of i) the stereoscopic intraoperative image pair or ii) the previous stereoscopic intraoperative image pair, and determining, by the computing device, a left-right disparity based on the first location and the second location.

In some embodiments, the element from the surgical field is at the desired depth. In some embodiments, the element is at a known depth relative to the desired depth in the surgical field, and wherein determining the left-right disparity is further based on a known calibration of a device that captured the stereoscopic image pair.

In some embodiments, the known depth relative to the desired depth is based on at least one of a typical anatomy of an eye, patient-specific preoperative diagnostic measurements of the eye being operated on, a 3D patient-specific model of the eye being operated on, and an input from a user.

In some embodiments, the left-right disparity is further based on a distance of a device that captured the left and right intraoperative images from at least one element in the surgical field, and wherein the at least one element is at a depth relative to the desired depth.

In some embodiments, the depth of the at least one element relative to the desired depth is based on at least one of a typical anatomy of an eye, patient-specific preoperative diagnostic measurements of the eye being operated on, a 3D patient-specific model of the eye being operated on, and an input from a user.

In some embodiments, the method further involves compensating, by the computing device, for an optical distortion of the cornea when determining the left-right disparity, wherein the optical distortion of the cornea is known from at least one of a typical anatomy of an eye, patient-specific preoperative diagnostic measurements of the eye being operated on, a 3D patient-specific model of the eye being operated on, and an input from a user.

In some embodiments, determining the left-right disparity is further based on selecting a region in the left intraoperative image and a region in the right intraoperative image. In some embodiments, determining based on the selected regions is based on cross-correlation of the left and right regions.

In some embodiments, the computing device determines a left-right disparity based at least on one of iOCT, and a tool tracker.

In some embodiments, the stereoscopic display is one of: a 3D monitor with or without glasses, a 3D head mounted display (HMD), or a binocular surgical microscope. In some embodiments, the method involves displaying via the stereoscopic display the left overlay superimposed with the left intraoperative image and the right overlay superimposed with the right intraoperative image.

In some embodiments, the surgical field includes an element that is to appear as above the single overlay, wherein at least one first portion in the left intraoperative image and at least one second portion in the right intraoperative image are associated with the at least one element, and wherein the method also involves displaying, via the stereoscopic display, the left overlay superimposed with the left intraoperative image such that an appearance of the left overlay in the at least one first portion of the left intraoperative image is different than the appearance of the left overlay outside of the at least one first portion of the left intraoperative image, displaying, via the stereoscopic display, the right overlay superimposed with the right intraoperative image such that an appearance of the right overlay in the at least one second portion of the right intraoperative image is different than the appearance of the right overlay outside of the least one second portion of the right intraoperative image, wherein the different overlay appearances cause the single overlay to appear as being below the element and being partially occluded by the element.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIGS. 6A and 6B are left and right images obtained via a stereoscopic imaging device showing examples of left-right disparity, according to some embodiments of the invention.

DETAILED DESCRIPTION

Figure 1:
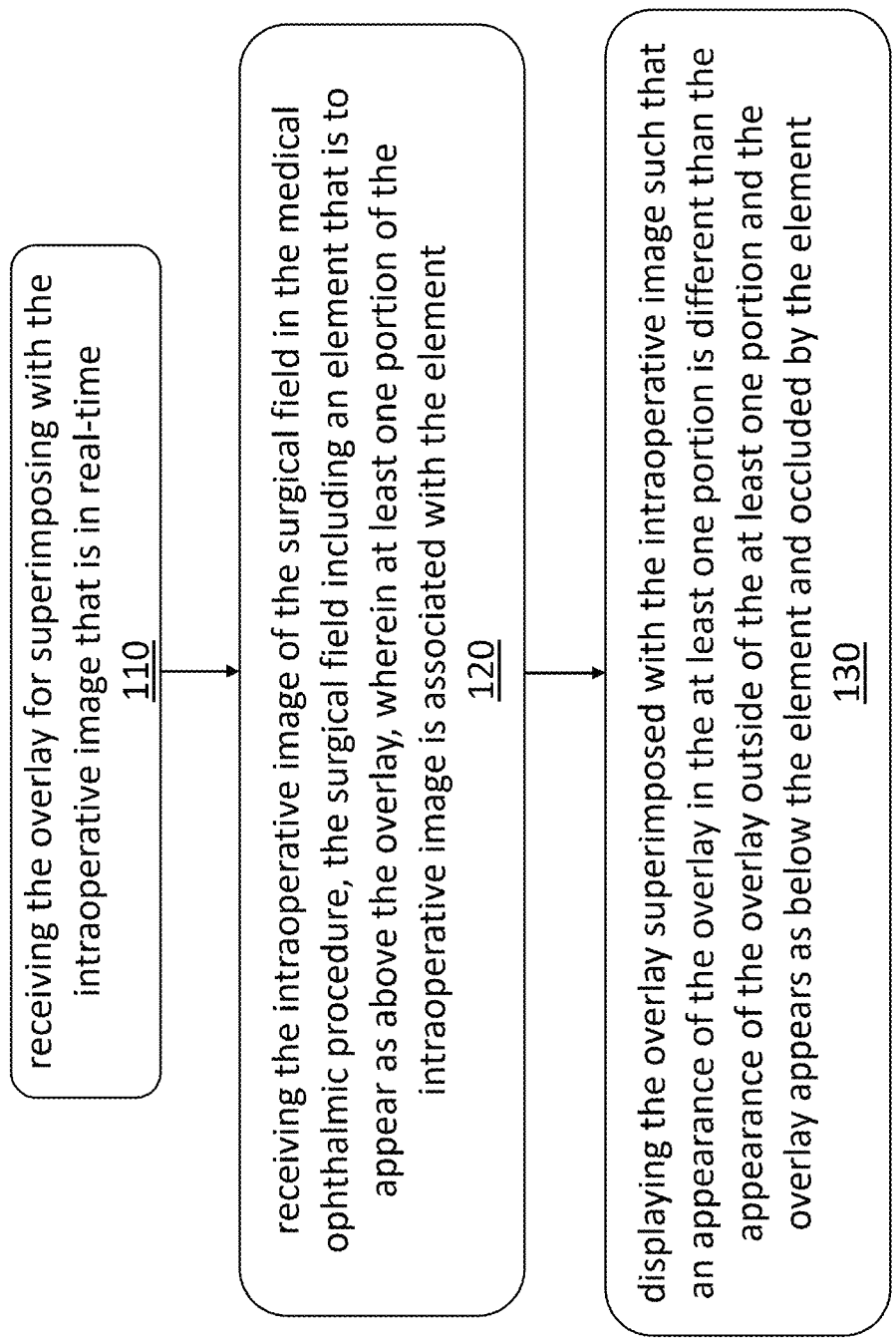
FIG. 1 is a flow chart for a method for displaying an overlay superimposed with an intraoperative image of a surgical field in a medical ophthalmic procedure, according to some embodiments of the invention.

In the following detailed description, numerous specific details are set forth in order to provide a thorough understanding of the invention. However, it will be understood by those skilled in the art that the invention can be practiced without these specific details. In other instances, well-known methods, procedures, and components, modules, units and/or circuits have not been described in detail so as not to obscure the invention.

Generally, the invention can involve displaying an image of a medical procedure (e.g., an intraoperative image) with additional information (e.g., data) that can augment the image of the medical procedure. The data can be an overlay and/or overlay data. The overlay data can be data that is used to represent and/or create the overlay. The overlay and/or the overlay data can be image data. The overlay can be shapes, information (e.g., guidance information), textual information, or any visual output that is desired to be displayed concurrent with or appear on top of the intraoperative image. In some embodiments, the overlay is textual information of numbers received from another device, such as a phacovitrectomy system. In some embodiments, the overlay is images, such as images of preoperative Optical Coherence Tomography (OCT) scans. In some embodiments, the overlay is information symbolic information (e.g., a number represented by a speedometer-like dynamic symbol).

In some embodiments, the overlay data is textual information that is settings and/or readings from another device (e.g., vital signs). In some embodiments, the overlay is input by a surgeon and is any information the surgeon wishes to view during the surgery. In some embodiments, the overlay data is locked to an anatomical element in the surgical field. In some embodiments, the overlay data is not locked to an anatomical element in the surgical field.

The overlay can be images that appear to be displayed concurrent with, displayed partially concurrent with, positioned partially on top, and/or positioned on top of the intraoperative image. In some embodiments, the overlay is displayed such that it is perceived by a user as being at a same depth as a depth the user is focused on within the surgical field. This can allow a user to avoid having to shift eye convergence in order to focus on the overlay. In some embodiments, the overlay can avoid occluding one or more elements in the surgical field (e.g., tools). The overlay can be displayed such that it varies in color, intensity, brightness, opacity, transparency, or any combination thereof.

In some embodiments, locations (e.g., one or more points) in images (e.g., intraoperative images, preoperative images) can be copied to other images obtained of the same surgical scenery (e.g., surgical field) such that the one or more points maintains their location relative to nearby elements in the scenery. For example, if an overlay is locked to a specific anatomy. In some embodiments, corresponding locations can be determined based on aligning the two images. A location can be an XY coordinate system location in the image, having sub-pixel resolution (e.g., non-integer x and y values). Each image can be defined as having pixels, pixel locations, and the pixel locations can be defined in an XY coordinate system. The location of points and/or objects within images can also be referred to in an XY coordinate system.

In some embodiments, the intraoperative image can be optical or digital. Overlay images can be superimposed on optical images, such as images viewed via oculars of a standard (e.g., optical) surgical microscope, by, for example, using a beam splitter that can be integrated into at least one of the microscope's optical channels.

Digital images can include pixels. Each pixel on the image to be displayed during the medical procedure can be assigned a value. The value for each pixel can depend on the intraoperative image and the overlay data. The overlay data can cause the pixels in the intraoperative image to be modified, according to the desired image output for the medical procedure. The intraoperative image can be obtained via a standard camera, microscope, endoscope, laparoscope, infrared (IR) camera, multi-spectral imaging, based on an optical coherence tomography (OCT) scan, and/or based on any intraoperative imaging modality. As is apparent to one of ordinary skill in the art, the intraoperative image can be a series of still images continuously changing in real-time.

When overlaying data with an intraoperative image, several factors can contribute to depth perception. Occlusion can be one cue used by the brain for depth perception. For example, when a first object partially occludes (e.g., obstructs) a view of a second object in an image, the second object can be perceived by a user as being behind the first object. An overlay that is superimposed on an intraoperative image such that it occludes a portion of the intraoperative image can be perceived by the user as being above an element in the surgical field that is represented by that portion of the image.

In ophthalmic surgery, when the surgeon is attending a capsule region of an eye, the surgeon may be using a tool or there can be other elements in the surgical field, that obstruct the surgeon's view of the capsule region in the intraoperative image (e.g., reflections from the cornea). When an overlay is presented over the portion of the intraoperative image showing the tool or over the portion of the intraoperative image showing the obstruction, the overlay can appear as being above the tool and above the obstructing element.

In another example, when an overlay is superimposed with an itraoperative image of a surgical field in a cataract procedure, the overlay may be presented over portions of the image that represent visible elements in the surgical field such as the iris, the sclera, a reflection from the cornea, and/or a tool. In this example, since the overlay partially occludes the portions in the image that represent these elements, the brain may interpret the overlay as being above these elements in the surgical field.

Eye convergence or stereoscopic vision can be cues that the brain uses for depth perception. In stereoscopic systems the user can be presented with two intraoperative images, one to the user's left eye and one to the user's right eye. Each visible element in the surgical field can have a corresponding left-right disparity. An element's left-right disparity can be referred to as a horizontal difference between a location of a portion of the image representing the element in the image displayed to the users left eye and the location of the corresponding portion (or generally corresponding portion) in the image displayed to the user's right eye. Two elements that have different disparities, corresponding to different convergence of the eyes when gazing at the representation of the elements in the images, can be perceived as being in different depths. And two elements that have the same disparity can be perceived as having the same depths.

The overlay and/or overlay data can be overlaid with an intraoperative image to avoid or substantially avoid obstructing particular portions of the image that display particular elements in the surgical field.

The overlay and/or overlay data can be overlaid with an intraoperative image pair as a stereoscopic overlay having a disparity that correspond to the disparity of the region the surgeon is attending.

In various embodiments, stereoscopic overlays are generated and/or superimposed with stereoscopic intraoperative images that have a left-right disparity that can allow for perception at any desired depth in the surgical field.

In general, an overlay can be received for superimposition with an intraoperative image. The overlay can be an overlay as described above. The overlay can be displayed such that it deviates from the received overlay in appearance, for example, as described below in FIG. 1.

FIG. 1 is a flow chart for a method for displaying an overlay superimposed with an intraoperative image of a surgical field in a medical ophthalmic procedure, according to some embodiments of the invention.

The method can involve receiving, by a computing device, the overlay for superimposing with the intraoperative image that is in real-time (Step 110). In various embodiments, the overlay is determined based on overlay data. In various embodiments, the overlay can be textual, images, live video, or an overlay as described above. The overlay can be locked or not locked to the anatomy. In various embodiments, the surgical field is of surgical procedures other than medical ophthalmic procedures.

The overlay data can be guidance information for the medical procedure determined during the capturing of a preoperative image. The guidance information can include a desired location and/or orientation for a medical object within respect to the preoperative image. The guidance information can be a desired location for insertion, placement and/or positioning of any kind of the medical object with respect to the patient. For example, the data can be xy coordinates of a center of a visual axis and an orientation, and it can be represented as a line centered and oriented per the data.

In some embodiments, the guidance information is a desired location for the surgical treatment. For example, the data can be a planned contour (e.g., an arc or a line) of an incision, a planned location of a biopsy, and/or a planned trajectory of a needle for use in a tumor ablation.

The guidance information can indicate an area and/or region of an eye. The guidance information can indicate a particular object in the preoperative image. The guidance information can have characteristics that can cause it to be displayed as a line, a dot, a series of dots, a color, or any visual indicator as is known in the art. In various embodiments, for an IOL placement, the guidance information indicates an orientation relative to the image for IOL placement and/or the desired IOL placement location.

In some embodiments, the guidance information is an enhancement of an anatomical element in the surgical field that is either visible or not visible in the intraoperative image. In these embodiments, the enhancement can be generated based on imageries from another device. For example, in an ophthalmic procedure, the enhancement can be of a membrane based on OCT scans (e.g. preoperative or intraoperative OCT scans). In another example, in brain surgery, the enhancement can be of a tumor based on MRI scans.

In some embodiments, the guidance information is received by the system. In some embodiments, the guidance information is automatically generated by a diagnostic device. In various embodiments, the overlay data is guidance information for the medical procedure that was determined based on measurements performed by a diagnostic device that captured an image (e.g., a 2D image) of the treated region, and/or based on 3D imageries generated by a diagnostic device. For example, in eye surgery, the 3D imageries can be generated by an OCT device. In another example in eye surgery, the 3D imageries can be generated by a Scheimpflug imager. In various embodiments, the overlay data is generated by an MRI, CT device, PET and/or ultrasound. In various embodiments, the overlay data is generated by any imaging device as is known in the art.

In various embodiments, if the guidance information is not automatically generated by a diagnostic device (e.g., such as the toric IOL location and orientation data), or if a surgeon chooses to change automatically generated guidance information, the surgeon can use a SW tool (e.g., a dedicated SW tool) for overlaying or drawing on the preoperative image any of the following: circles, lines, other geometrical shapes, and/or freehand drawing. The overlays can indicate areas by shapes filled. e.g., by texture and/or color. The SW tool can store the overlay as textual data that is used during a procedure to generate an overlay on the intraoperative image. For example, guidance information for a capsulotomy can be a circle having a known center location and diameter drawn as an overlay with the preoperative image.

In various embodiments, the overlays are drawn on an intraoperative image (e.g., a continuous live image or a snapshot), so that a surgeon can plan a surgery to perform or as a plan to teach another person to perform, in supervisory or residential capacity.

In some embodiments, the overlays are pre-planned based on 3D data (e.g., using 2D slices, 3D segmentations and/or volume rendering). In these embodiments, the preplanning information is determined in a coordinate system of the 3D data. In some embodiments, during a surgery the overlay is generated by rendering the preplanning information from the point-of-view (POV) of the camera.

In some embodiments, the overlay is an enhancement of anatomical elements in the 3D imageries (e.g., such as a tumor and/or a vertebra). In some embodiments, the overlay is generated for example by rendering 3D segmentations (e.g. 3D models) of the anatomical elements from the POV of the camera. In some embodiments, the POV of the camera is determined based on a navigation system. The navigation system can track a patient and a camera using a tracking system, and the coordinate system of the 3D data can be registered to the patient.

In various embodiments, the guidance information is a guidance information for an intraocular lens (IOL) placement, a guidance information for a capsulotomy, a guidance information for an incision, an enhancement of a membrane or part of a membrane, an enhancement of a capsule or part of a capsule, or any combination thereof.

In some embodiments, the overlay is 3D data or based on 3D data. The 3D data can be MRI or CT (e.g. for brain or spine surgery) and/or OCT (e.g. for ophthalmic surgery). The 3D data can be 3D data based on any imaging device capable of generated 3D data is known in the art. In some embodiments, the 3D data is acquired preoperatively. In some embodiments, the 3D data is acquired intraoperatively. In various embodiments, the overlay is a rendered image of the 3D data (e.g. volume rendering) or of a three-dimensional model.

In some embodiments, 3D data is segmented and the segmented 3D model is rendered to generate an overlay. For example, a 3D segmentation of a membrane can be generated from 3D OCT data. The contours of the membrane in a rendered image of a 3D model of the membrane can be copied to an intraoperative image based on an image of a retina that is captured concurrently with the OCT scan. In another example, a 3D model of a posterior capsule based on OCT or a Scheimpflug imager can be segmented.

In some embodiments, the overlay is based on image registration between an image having guidance information to an intraoperative image. In some embodiments, the overlay is based on image registration between a first image that is a preoperative image and a second image that is an intraoperative image. For example, for eye surgery the first image can be a preoperative image of the eye and the second image can be the intraoperative image. In various embodiments, for other types of surgeries (e.g., brain, spine and/or laparoscopic surgery), the first image can be a rendered image of a 3D model generated from 3D imageries (e.g., MRI and/or CT), and the guidance info is another rendered image of preplanning determined based on the 3D data or segmentations from the 3D data, that was rendered from the same POV. For example, the first image can be a rendered image of a model of the outer surface of the cortex from CT/MRI that is registered to the intraoperative image (e.g. based on sulci, gyri, blood vessels that can appear in the 3D model), and then the same registration can be used to copy an augmentation from another rendered image (e.g., generated from the same POV), a rendering of a superficial tumor that is just below the surface of the cortex, such that all the rendered 3D models have the same coordinate system of the 3D data.

Another example, for a laparoscopic procedure of the liver, the first image can be a rendered image of a model of a surface of the liver as generated from MRI.

The overlay can be determined based on a preoperative or intraoperative image of an eye, a preoperative or intraoperative OCT scan, a user input or any combination thereof.

The overlay can be guidance overlay for an intraocular lens (IOL) placement, a guidance overlay for a capsulotomy, a guidance overlay for an incision, an enhancement of a membrane or part of a membrane, an enhancement of a capsule or part of a capsule, or any combination thereof.

The overlay can be flat overlay or a 3D overlay. For example, the overlay can be an oblique line or a wireframe cage. The overlay can appear at a single depth within a three-dimensional view. The overlay can be an overlay spanning multiple depths within a three-dimensional view.

The method can involve receiving, by a computing device, the intraoperative image of the surgical field in the medical ophthalmic procedure, the surgical field including an element that is to appear as above the overlay, wherein at least one portion of the intraoperative image is associated with the element (Step 120).

The intraoperative image can be an image of a surgical procedure during the surgical procedure. The intraoperative image can be a real-time image, live image, snapshot image, and/or still image. The real-time image and/or live image can be an image that shows the surgical field while the surgeon is performing the surgery. The real-time image and/or live image can be an image of the surgical field that is aimed to be presented to the surgeon within a time frame that it does not negatively impact the surgeon's ability to perform the procedure. For example, a real-time image can be presented to the surgeon with a delay of less than 20 milliseconds. In some embodiments, the delay is less than 100 milliseconds. The intraoperative image can be a snapshot of the surgery. For example, the surgeon may want to see a snapshot of the surgical field at the beginning of a surgery to refer to during the surgery.

The intraoperative image can include one or more portions that are associated with an element in the surgical field that are desirable to have appear above the overlay. For example, the intraoperative image can have portions that depict an iris, tools, a corneal reflection, an air bubble, a portion of a hand, a lens fragment and/or any element that is visible in the actual real life surgical field. A tool can be any tool a surgeon can use.

The intraoperative image can be obtained with a digital microscope or an optical microscope or any combination thereof.

Figure 2B:
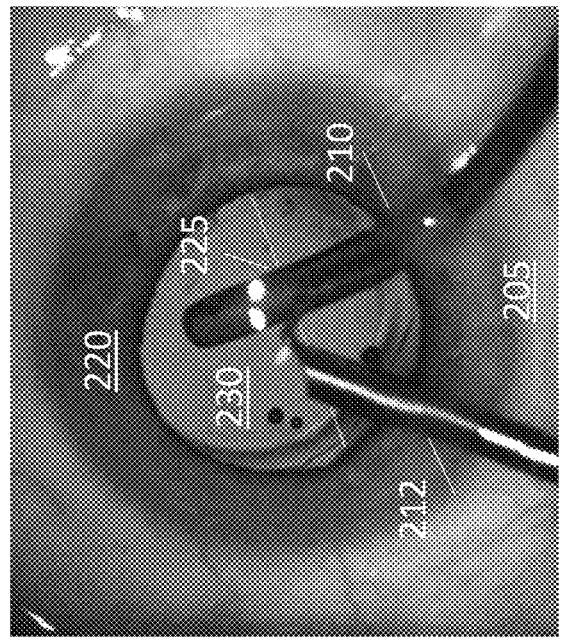
FIG. 2B is an example of the intraoperative image of the surgical procedure having the same three portions of FIG. 2A, according to some embodiments of the invention.
Figure 2A:
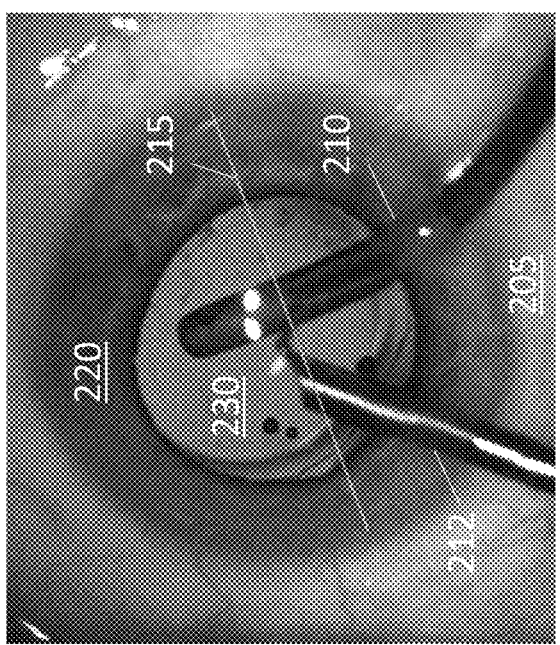
FIG. 2A is an example of an intraoperative image of a surgical field having three portions, a first portion that is a tool, a second portion that is a tool, and a third portion that is an iris that are to be appear above an overlay, according to some embodiments of the invention.

In various scenarios, it can be desirable to have one or more portions to appear as being above the overlay. For example, turning to FIG. 2A, FIG. 2A is an example of an intraoperative image 205 of a surgical field having three portions, a first portion that is a tool 210, a second portion that is a tool 212, and a third portion that is an iris 220 that are to be appear above an overlay 215, according to some embodiments of the invention. In FIG. 2A the overlay 215 is displayed with the intraoperative image 205 such that its appearance is the same in all the image portions it is superimposed on. For example, the overlay 215 partially occludes the portions of the intraoperative image of the tools 210 and 212 and the iris 220. The overlay 215 is also displayed above the portion of the intraoperative image of the pupil 230. This can have the effect of giving a user (e.g., surgeon or other person viewing the procedure) a 3D perception that the overlay is above the tools 210 and 212 and the iris 220. In this scenario, it can be desirable to display the overlay 215 such that it appears to the user as being below the tools 210 and 212 and the iris 220, or in other words it can be desirable to display the overlay such that the portions of the intraoperative image of the tools 210 and 212 and the iris 220 appear as being above the overlay 215.

Turning back to FIG. 1, the method can involve displaying, by the computing device, the overlay superimposed with the intraoperative image such that an appearance of the overlay in the at least one portion is different than the appearance of the overlay outside of the at least one portion and the overlay appears as below the element and occluded by the element (Step 130). For example, turning to FIG. 2B, FIG. 2B is an example of the intraoperative image 205 of the surgical procedure having the same three portions of FIG. 2A, tools 210 and 212, the iris 220. In FIG. 2B the overlay 225 is displayed outside of portions of the tools 210 and 212 and the portion of the iris 220 differently then it appears inside of the portions, such that the tools 210 and 212 and the iris 220 appear as obscuring the overlay 225, and the overlay 225 appears as being under the elements 210 and 212 and 220, according to some embodiments of the invention. In particular, in this example, the overlay 220 is displayed outside of the portions of the tools 210 and 212 and the iris 220 as a line having a white color, and not displayed inside of the portions, such that the appearance of the overlay 220 outside of the portions and inside of the portions is different.

In some embodiments, displaying the overlay differently involves presenting the overlay with a different pattern inside of the portion versus outside of the portion. In some embodiments, displaying the overlay differently involves presenting the overlay with a different color inside of the portion versus outside of the portion. In some embodiments, displaying the overlay differently involves presenting the overlay with a different transparency inside of the portion versus outside of the portion. In some embodiments, displaying the overlay differently involves presenting the overlay only outside of the portion.

Superimposing an overlay on an image can involve modifying pixels of the image. For example, to superimpose line 215 on image 205 in FIG. 2A, pixels of image 205 that are along the line can be modified. In various embodiments, pixels in the intraoperative image effected by the overlay can be wholly replaced and/or modified, such that the desired visual output for the overlay in the intraoperative image is achieved. Modifying a pixel can involve changing its gray level (e.g., in a monochromatic image) or changing its RGB values (e.g., in a color image). For example, the pixel's RGB values can be modified such that the green (G) value is increased (e.g., by 50 and/or without surpassing the maximal allowed value), while the red (R) and blue (B) values are not modified. In this example, the overlay can appear as being green and transparent. In another example, the pixel's RGB values are replaced by [100, 100, 100]. In this example the overlay appears as white and opaque. In various embodiments, the overlay is not uniform, and different pixels may be modified differently. In various embodiments, the overlay is uniform and different pixels are modified uniformly.

Displaying the overlay differently inside of the portion versus outside of the portion can involve modifying pixels of the intraoperative image that are inside of the portion (e.g., only those pixels that are to be affected by the overlay) in one manner and modifying pixels of the intraoperative image that are outside of the portion (e.g., only those pixels that are to be effected by the overlay) in a second manner. In some embodiments, a pixel can be modified according to a set of rules. The set of rules can be different for pixels in the portion and pixels outside the portion.

For example, turning to FIG. 2A and FIG. 2B, line 215 is an overlay superimposed with image 205. FIG. 2A illustrates how the overlay 215 appears when the method of FIG. 1 is not implemented. By applying the method of FIG. 1, the overlay is received. The overlay can be two points in the coordinate system of the intraoperative image that define two edges of a previously determined line, a line thickness, a line color and brightness, and a transparency flag. Each pixel in the intraoperative image that falls within or along the boundaries of the defined line (e.g., since the line has a thickness, a pixel may fully be within the contour, or partially within it, when it is located just along the line contour), can be classified as being inside portions 210, 212 or 220, or outside of these portions. Based on the classification, the pixels were either modified (e.g., when they were classified as being outside these portions) or not modified (e.g., when they were classified as being inside these portions), resulting in overlay 225, that appears as being occluded by the elements represented by these portions and being below them.

In some embodiments, the intraoperative image is an optical image. The optical image can be directly viewed by the surgeon. For example, the optical image can be viewed via an ocular of a surgical microscope. In these embodiments, a digital image of the optical image can be obtained by a camera that is assembled with the surgical microscope (e.g. integrated in the microscope with a beam splitter, so that a live image of the surgical field can be acquired from the same (or substantially the same) perspective as the surgeon viewing the optical image of the surgical field via the ocular). In these embodiments, an overlay image can be injected into the optical path that the surgeon views, for example via a display device and a beam-splitter. The overlay alone, without the intraoperative image, can be projected as an overlay image into the optical path that the surgeon views. When viewing the optical image with the superimposed overlay image, black pixels in the overlay image can appear as invisible and only non-black pixels in the overlay image can be seen, appearing as a semi-transparent overlay superimposed with the intraoperative (optical) image.

In some embodiments, an overlay or overlay data for superimposing with the optical image can be received. In some embodiments, the overlay is determined based on the live image from the camera (e.g., when the overlay is a guidance overlay that is to appear as locked to the anatomy).

In some embodiments, the overlay can be determined independently of the live image from the camera (e.g., when it is a preoperative OCT scan for superimposing with the intraoperative image as a Picture-In-Picture).

In some embodiments, the visible elements in the surgical field can appear as being above the overlay. In these embodiments, parts of the overlay image can be replaced by black pixels such that when the surgeon views the optical image with the superimposed overlay image, the overlay does not occlude the visible elements.

In general, the appearance of the overlay over portions of the optical image that are associated with the visible elements can appear differently than the appearance of the overlay over portions of the optical image that are not associated with the visible elements, such that the visible elements appear as being above the overlay. Both the camera and the display can be digitally aligned (e.g., pre-calibrated) to the optical view, such that the overlay can be superimposed at the correct location over the optical image. In some embodiments, the appearance of the different parts of the overlay is determined based on the digital image. In various embodiments, the overlay can be displayed with an optical image in any optical system having an integrated camera that can capture an image of the FOV that the user is viewing and a capability to superimpose an overlay on the optical image that the user views.

For embodiments of the invention where the user is viewing an optical intraoperative image (e.g., via a surgical microscope), a digital image of the optical image can be acquired (e.g., acquired with a beam splitter) and used as the basis for determining the overlay appearance. Accordingly, the embodiments described herein using segments and pixels to determine and/or generate the overlay appearance on the intraoperative image apply to the optical intraoperative image embodiments.

In various embodiments, pixels of the intraoperative image are classified as being inside or outside of the portion. In some embodiments, the classification is based on the intraoperative image, a previous intraoperative image, or any combination thereof. The previous intraoperative image can be a previous frame of the intraoperative image. For example, if the intraoperative image is frame n, the previous frame can be n−1, or n−m, where m is any integer value.

In some embodiments, the classification is based on the color (e.g., RGB value, or color value, or value) of the pixel in the intraoperative image (e.g., pixel-based). In some embodiments, the classification is based on the value of the pixel and the value of neighboring pixels. In some embodiments, the classification is performed based on segments derived from segmenting the intraoperative image. In some embodiments, the classification is performed based on a disparity determination. In various embodiments, the classification is based on intraoperative OCT. In some embodiments, the classification is based on a tool tracker.

In some embodiments of pixel-based classification, each pixel in the intraoperative image (e.g., the image before adding the overlay) can be evaluated based on a predefined criteria. The predefined criteria can be based on procedure type. For example, the predefined criteria can indicate that a toric IOL alignment symbol (e.g., the guidance overlay) can be overlaid only over red pixels in the intraoperative image (e.g., the red appearance can be due to the red-eye effect that may be generated by the reflection of coaxial illumination from the retina). Overlaying only over red pixels can be the predefined criteria, for example, if the system operates under the assumption that non-red pixels originate from tools or corneal reflections.

In some embodiments, only pixels that have a color within a range of colors are overlaid. For example, only pixels that have a color within a range of red hues that are reflected from the patient's retina are overlaid. In some embodiments, during pixel-based classification, pixels that have a color within a range of colors are not overlaid. For example, pixels that have a color within a range of hues that were predetermined to indicate a tool are not overlaid. In some embodiments, during pixel-based classification, pixels that have a brightness within a predetermined range are not overlaid. For example, pixels that have a brightness above a value that was predetermined to indicate corneal reflections are not overlaid.

In some embodiments, the classification can be based on the pixel value and on values of surrounding pixels. For example, a pixel can be classified as meeting the criteria of having a red appearance if the average color of the pixel and its surrounding (e.g., neighboring) pixels is within the range of red hues that is set as the predetermined criteria. This can be useful when the background is less uniform, for instance during an open brain procedure when the average color of the exposed tissue is different than the color of a tool. The size and shape of the surrounding neighborhood around the pixel that is used for classifying the pixel may be part of the predetermined criteria.

In some embodiments, a mask image (e.g., an image of zeros and ones) is generated based on the predetermined criteria and according to the values of corresponding pixels, that can be filtered and/or smoothed (e.g., to close small holes in the mask). In some embodiments, classifying a pixel as being inside or outside of the portion can be performed based on the mask. For example, the mask image can have the same dimensions (or substantially the same dimensions) as the intraoperative image. As another example, the mask image can be generated only for a region around the overlay.

In some embodiments, the predetermined criteria are periodically updated. For example, the predetermined criteria may be determined by a processor based on a previous frame of the live video, and the processor may use the updated criteria when generating the overlay for the current frame. Updating the predetermined criteria can be important for example when the appearance of the background changes. For example, the surgeon may change the level of illumination, or the patient may change the eye's gazing direction, which can change the hue of red in the background.

In various embodiments, the classification is based on color represented as RGB, HSV, LAB and/or Ycbcr, or any color code known in the art. In various embodiments, the classification for monochromatic images is based on gray-level.

In some embodiments, classification of the pixels is segmentation-based. The intraoperative image can be segmented into segments (e.g., via image segmentation as is known in the art). In some of these embodiments, the segments can be classified. For example, deep neural networks can be used to segment the image and to classify each segment as one of several predefined elements, such as pupil, iris, sclera, tools, air bubbles, corneal reflections, and/or any object in the surgical field. One or more segments can be associated with elements of the surgical field that are not to be obscured. For each type of overlay (e.g., guidance for IOL placement or guidance for LRI) rules can be predefined such that specific classes of segments appear as occluding the overlay. For example, the iris can be defined as always being an occluding segment for an IOL placement guidance overlay and always being an occluded segment for an LRI guidance overlay.

In some embodiments, pixels within the boundaries of these segments can be classified as being inside the at least one segment. The overlay can be displayed differently inside of and outside of the one or more segments, as described above with respect to the portions of the intraoperative image. For example, the intraoperative image can be segmented into classified segments, and the overlay can be limited to being displayed as a colored line outside of the iris and tool segments, and not displayed inside of the iris and tool segments.

In some embodiments, inner and/or outer margins can be added to segments, for example to improve overlay visibility and/or to prevent the overlay from breaching the segment boundaries.

The breaching can happen due to, for example, the segmentation being determined based on a previous frame of the image, and when there is, for example, fast movement in the image such that the segment boundaries used are not up to date, and therefore not accurate. This can occur, for example, if a tool is moved, or the eye gaze changes. The inner/outer margins can prevent the breaching since there can be a limit to an amount of segment movement that can occur in the short time interval that takes for the segmentation to complete.

In some embodiments, when a stereoscopic intraoperative image-pair is acquired and displayed, disparities of segments (e.g., segments determined during image segmentation) can be calculated. A disparity of a segment is the difference between a location of the segment in the image that is displayed to the user's left eye, and the location of the same segment in the image that is displayed to the user's right eye. A disparity of a segment can be calculated for segments that are determined in both images of the intraoperative image-pair (left-right disparity and its correspondence with depth in the surgical field is described in detail further below). A determination as to whether a segment is to appear as being above or below the overlay can be based on a particular segment's disparity relative to the disparity that is used when generating the overlay (e.g., the disparity of a stereoscopic overlay can correspond to a desired overlay depth, as described further below). Pixels within the segment can be classified as belonging to an occluding portion of the image or not based on this determination. In some embodiments, classifying a pixel as belonging to an occluding portion of the image or not is based on the pixel's disparity. A determination as to whether a pixel is to appear as being above or below the overlay can be based on a particular pixel's disparity relative to the disparity that is used when generating the overlay. For example, the pixel's disparity is determined based on the disparity of a segment that the pixel is part of. As another example, the pixel's disparity can be determined based on the disparity of a part of a segment that the pixel is part of, as described below.

In some embodiments, an image segment (e.g., a segment associated with an element in the surgical field) can have a different disparity in different parts of the segment, and the classification will change for different parts of the segment. For example, a tip of a tool may be deeper in the eye relative to a proximal part of the tool, for instance the part of the tool where the tool penetrates the eye. A disparity can be determined for distinct points of a tool (e.g., the tooltip and/or an entry point of the tool to the eye, that can be identified in both images of the stereoscopic image-pair), and based on that, the disparity can be determined for various points in the tool (e.g., the disparity for different points along a straight tool can change linearly). In some embodiments, a known 3D model of a tool can be used when determining the disparity for various points in the tool (e.g., the type of a tool can be determined by deep learning). Pixels in the tool segment can be classified as belonging to an occluding portion of the image or not based on comparing their disparity to the disparity that is used when generating the stereoscopic overlay. Parts of the tool that are above the desired depth of the overlay (e.g., as determined from their disparity) can appear as occluding the overlay and as being above the overlay, and parts of the tool that are below the desired depth of the overlay can appear as occluded by the overlay and as being below the overlay.

In some embodiments, the overlay represents a three-dimensional entity. In some embodiments, parts of an overlay can appear as occluding an element in the surgical field, while other parts can appear as being occluded by the same element. In these embodiments, a disparity of the segment (or separately for different parts of a segment) can be determined and compared to the disparity that was used for generating the different parts of the overlay.

For example, in eye surgery, an overlay can be a wireframe cage for guiding IOL placement. The wireframe cage overlay can be displayed such that a tooltip that is located within the volume of the virtual cage occludes the posterior part of the virtual cage, while at the same time being occluded by the anterior part of the virtual cage.

In some embodiments, the classification can be based on an intraoperative OCT scan. In some embodiments, an alignment between an intraoperative OCT and a camera used to obtain the intraoperative image is used for the classification. Using the OCT, pixels in the intraoperative image can be associated with relative depths in the surgical field, and based on the relative depth a pixels can be classified as being above or below the desired depth of the overlay (e.g. the depth the overlay is intended to appear as being in). A threshold surface (e.g. a virtual surface) in a volumetric OCT scan can be defined that is equivalent to a surface of the overlay (e.g. the intended overlay surface can be three-dimensional). Columns in the OCT scan (e.g., each A-scan) can correspond to pixels in the real time image (e.g., based on the alignment between the intraoperative OCT and the camera), and a depth that is associated with a pixel relative to the threshold surface can be determined based on a corresponding OCT A-scan. There is typically a function that correlates A-scans with pixels, and the correspondence is not necessarily integer.

In some embodiments, classification is based on a tool tracker. A tool tracker can include optical tracking, electromagnetic tracking, or any other tracking technology that can track a tool during surgery as is known in the art. In some embodiments, an alignment between the coordinate system of the tool tracker and a camera used to obtain the intraoperative image is used for the classification. In some embodiments, classification is based on a relative position and orientation between the tool and the camera that generated the intraoperative image. Based on the relative position and orientation, a pixel can be associated with the tracked tool. Moreover, a pixel can be associated with a known point of the tracked tool, and therefore each pixel that is associated with the tracked tool can be separately classified as being above or below a desired depth of the overlay. In some embodiments, the association is based on a known 3D model of the tool.

In some embodiments, the classification is both pixel-based and segmentation-based. For instance, segments that are determined to be associated with the iris or with the sclera can appear as occluding the overlay (e.g. the overlay may be limited to appear only within the segment associated with the pupil), so all pixels within these segments can be classified as belonging to an occluding portion of the image (e.g., segmentation-based classification). Pixels having a color hue that is not within a range of red hues (e.g. pixels within portions associated with a tool or with a corneal reflection) can also be classified as belonging to an occluding portion of the image (e.g. pixel-based classification).

In some embodiments, segmentation-based classification can be used for determining that an overlay should not be superimposed with a pixel, even if the pixel is not within an occluding portion of the image. For example, an overlay may be limited to a segment associated with an IOL (e.g. an IOL that the surgeon has inserted into the capsular bag of the patient's eye). In this example, the overlay is not superimposed with pixels that are classified as being in the pupil segment but not in the IOL segment.

Figure 3A:
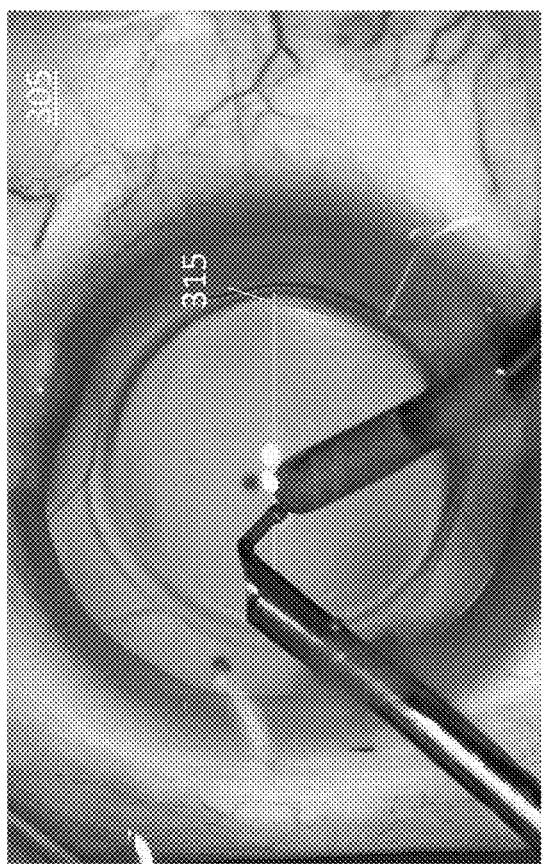
FIGS. 3A and 3B are examples of an intraoperative image of an ophthalmic surgical procedure of an IOL insertion, according to some embodiments of the invention.
Figure 3B:
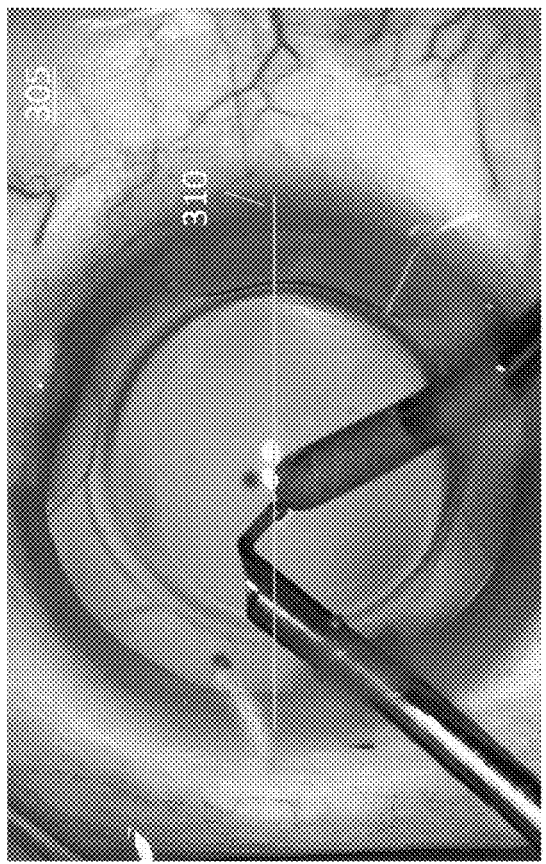

FIGS. 3A and 3B are examples of an intraoperative image 305 of an ophthalmic surgical procedure of an IOL insertion, according to some embodiments of the invention. As can be seen in FIG. 3A, an overlay 310 is displayed with the intraoperative image 305 where the overlay appearance is the same for all pixels. FIG. 3B shows the intraoperative image 305 having an overlay 315 appearance that varies for different pixels of the image (e.g., as described above in FIG. 1). In FIG. 3B, the overlay is limited to the segment that is associated with the IOL, and the overlay also appears as being occluded by the tools and the corneal reflections, and as being below them. During the procedure the IOL can shift to an off-center location where it is partially hidden below an iris 330. In this manner, the overlay can be limited by pupil boundaries on one side and by IOL boundaries on the other side (not shown).

Figure 4C:
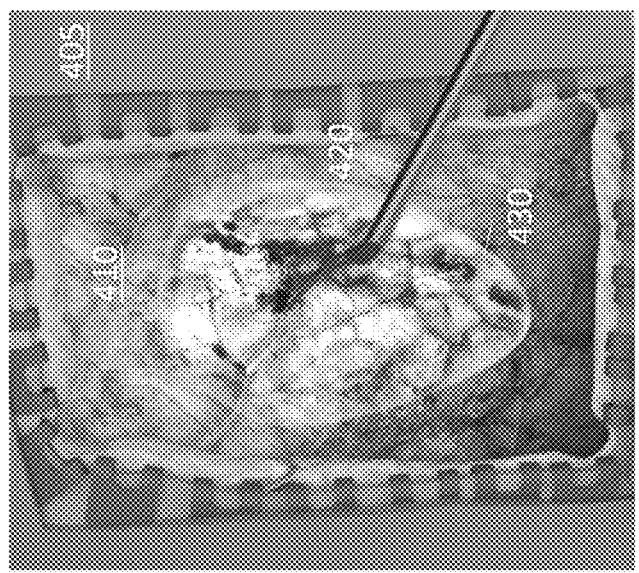
FIGS. 4A, 4B and 4C are an intraoperative image of a brain surgery, according to some embodiments of the invention.
Figure 4B:
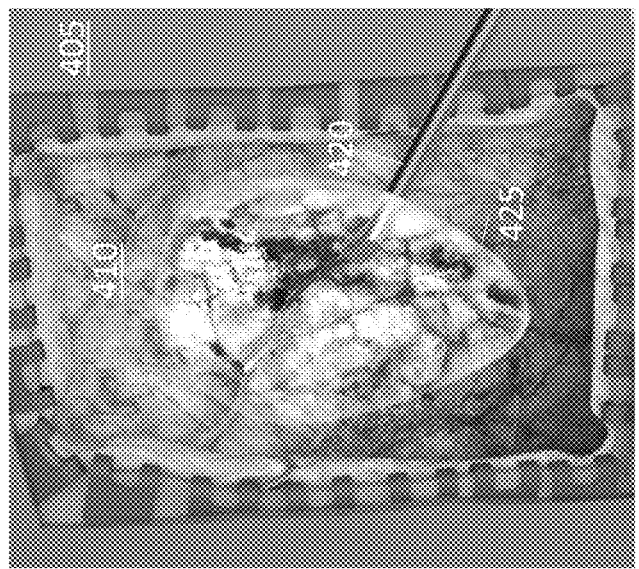
Figure 4A:
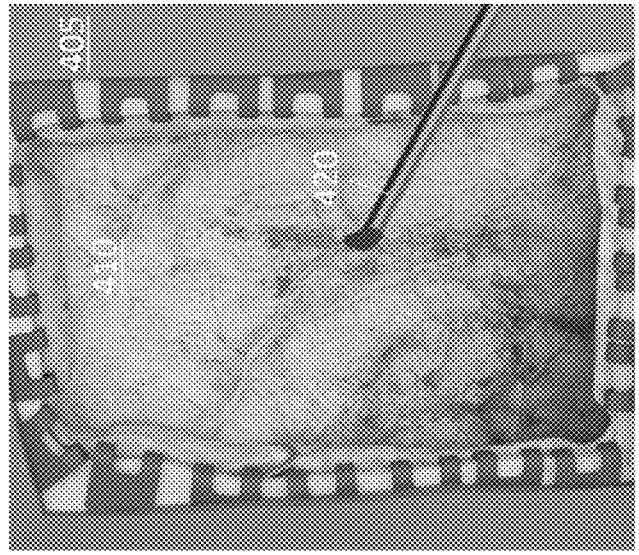

In various embodiments, the surgical procedure can be a brain surgery and the intraoperative image can be a surgical field of the brain surgery. In various embodiments, the surgical procedure can be any type of surgery. For example in brain and/or spine surgeries, the overlay can be guidance information of parts of anatomy that at least a part of which cannot be seen in the intraoperative image and that are important for a surgeon to know where they are. As another example, the overlay can be guidance information and/or preplanning overlays that can indicate for example, locations of incisions and/or trajectories for inserting a tube or a needle. Turning to FIGS. 4A, 4B and 4C, FIGS. 4A, 4B and 4C are an intraoperative image 405 of a brain surgery, according to some embodiments of the invention. FIG. 4A shows an intraoperative image 405 of a brain surgery with a brain 410 and a tool 420 in the surgical field (e.g. the tool is located above the surface of the cortex). FIG. 4B shows the intraoperative image 405 of a brain surgery with a brain 410 and a tool 420 in the surgical field. The intraoperative image 405 is provided with the overlay 425 where the overlay 425 has an appearance that is the same for the entire intraoperative image. The overlay represents a tumor that is located under the surface of the cortex. It is superimposed with image 405 in a transparent manner, such that the surface of the cortex appears to be transparent and above the overlay. However, although the overlay is transparent it can appear as if the overlay obstructs the tool 420 and it can appear that the overlay is above the tool. This is in contradiction to the appearance of the overlay as being below the surface of the cortex (e.g. the different appearances of the cortex and the tool relative to the overlay can be attributed to several factors, such as the fact that the tool is moved by the surgeon as opposed to the static cortex). FIG. 4C shows an intraoperative image 405 of a brain surgery with an overlay 430 that is displayed differently within a portion in the intraoperative image (e.g. within the portion associated with the tool 420) and outside of the portion, such that the tool 420 appears as above the overlay 430.

Figure 5B:
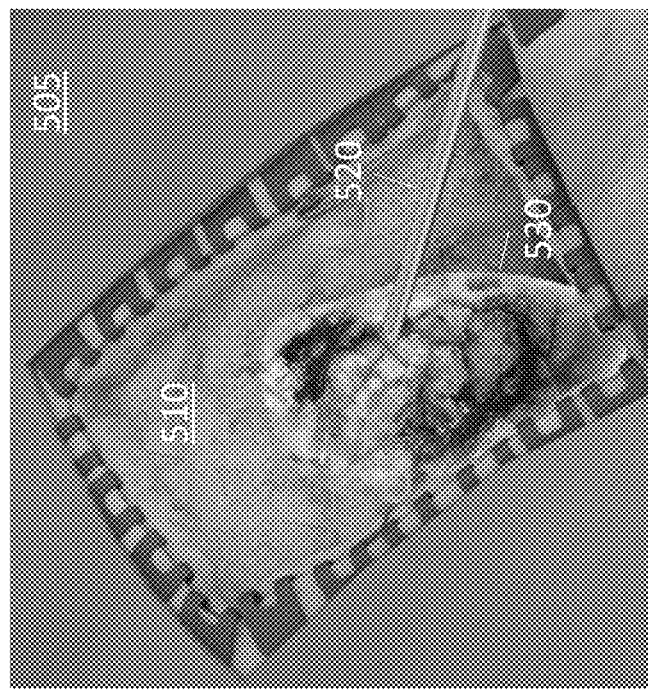
FIGS. 5A and 5B are an intraoperative image of a brain surgery, according to some embodiments of the invention.
Figure 5A:
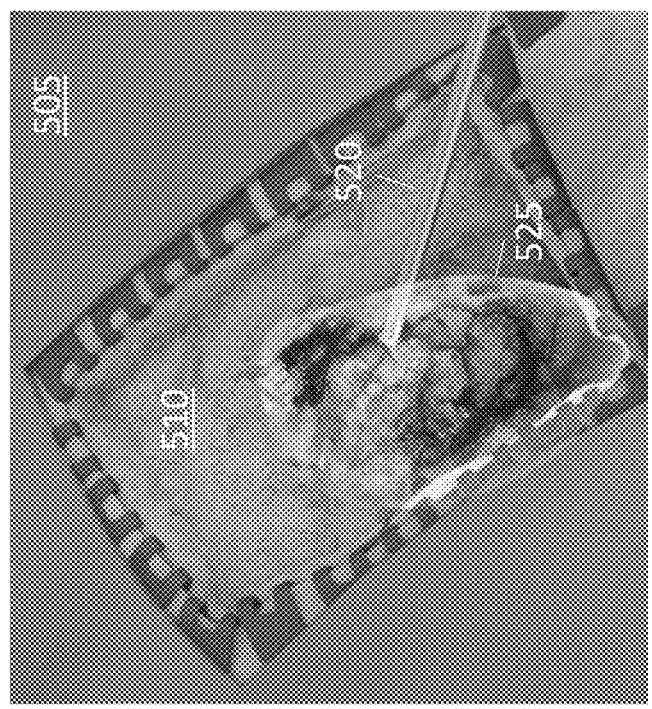

FIGS. 5A and 5B are an intraoperative image 505 of a brain surgery, according to some embodiments of the invention. FIG. 5A shows an intraoperative image 505 of a brain surgery showing a brain 510 and a tool 520 is in the surgical field. The intraoperative image 505 is provided with the overlay 525 where the overlay 525 has an appearance that is the same for the entire intraoperative image, such that the overlay obstructs the tool 520 and it appears that the tool is under the overlay. The overlay also obstructs areas that are outside the opening in the skull (e.g. the area where a craniotomy was performed) and it can appear as if the overlay is above the skull. FIG. 5B shows an intraoperative image 505 of a brain surgery with an overlay 530 that is displayed differently within portions in the intraoperative image and outside of the portions, such that the tool 520 and the skull appear as being above the overlay 530.

In various embodiments, the surgery can be for example open brain or spine surgery, endoscopic brain or spine surgery, minimally invasive brain or spine surgery, otorhinolaryngology surgery, orthopedic surgery, laparoscopic surgery, general surgery, vascular surgery or dental surgery.

Several cues can contribute to depth perception. As described above, an image element that is partially obscured by another image element can be perceived as being behind it. In another example, for systems that obtain an image stereoscopically, image elements having different relative disparities in the two images (e.g., the left and right images), corresponding to different convergence of the eyes when gazing at the image elements, can be perceived as being in different depths.

Left-right disparity can be a horizontal difference between a location of an image element in the image displayed to the user's left eye and the location of the same image element in the image displayed to the user's right eye.

In some embodiments for stereoscopic image output, a stereoscopic overlay is displayed as an overlay with an intraoperative image for a left eye ("left intraoperative image") and as an overlay with an intraoperative image for a right eye ("right intraoperative image"). In some embodiments, displaying an overlay in a three-dimensional (3D) view can be implemented by displaying the overlay in each of a left and right image, such that the overlay has the same (or substantially the same) left-right disparity as the region in the surgical field that the surgeon is attending (e.g. as represented by elements in the left and right images). For example, an overlay can be an image, data and/or numbers that is displayed at the same depth that the surgeon is attending, so it is, for example, comfortable on the eyes of a user to view (e.g. the surgeon can switch her or his attention between the anatomy and the overlay without a substantial change of eye convergence). The overlay can also be displayed with a different disparity, as long as the difference between the disparity of the region that the user is attending and the overlay disparity isn't too large. The maximal disparity difference that can still allow for comfortable viewing of both the anatomical region and the overlay can vary from person to person. For example, a disparity difference that is equivalent to a 1 mm difference in depth can be comfortable for one person while it may be uncomfortable for another person. In these embodiments, for example, a location of the overlay can be determined for one of the images (e.g., the left image or the right image) and then the location can be determined with respect to the other image such that it has a desired disparity.

Typically, the difference between the x locations of the overlay in the left and right images can contribute to the comfort of viewing. For example, an overlay can be superimposed in any location [X1, Y1] in the left image, as long as it is superimposed at location [X1-D, Y1] in the right image, where D is the disparity of elements in the region the surgeon is attending.

In some embodiments, displaying a guidance overlay in a 3D view can be implemented by displaying the overlay in each of a left and right image, such that the overlay has the same (or substantially the same) left-right disparity as the image elements that the guidance overlay refers to. In the toric IOL alignment example, the surgeon can align the IOL to the overlay, so it can be desired that the overlay has the same left-right disparity as the IOL. This can allow a surgeon to simultaneously and comfortably view both the IOL and the overlay.

In some embodiments, guidance overlay for a surgical procedure can be displayed as locked to the anatomy. For instance in ophthalmic surgery, an overlay for guiding IOL placement can move and/or rotate corresponding to movement and/or rotation of the patient's eye. In some embodiments for guidance overlay, an overlay location and/or orientation can be determined with respect to a reference image. For example, the reference image can be a preoperative image from a diagnostic device.

As described above, during the surgical procedure the overlay location and/or orientation with respect to an intraoperative image can be continuously determined by copying locations of the overlay from the reference image to the intraoperative image. As described above, copying locations of the overlay can involve copying (e.g., one or more points) in one image of a scene to another image obtained of the same scene (e.g., surgical field) such that the one or more points maintains their location relative to nearby elements in the scene. This can be implemented, for example, based on image registration and/or as described in co-pending Patent Cooperation Treaty Application, PCT/IL2020/051090 filed Oct. 11, 2020.

One way for generating a stereoscopic guidance overlay that is locked to the anatomy is to determine the overlay for the left intraoperative image and independently determined for the right intraoperative image. The overlay can be separately copied from the reference image to each of the left and right intraoperative images.

When copying locations (e.g. an overlay location) from a preoperative image to a stereoscopic intraoperative image-pair, errors can be caused due to the gazing direction of the patient's eye. The reference image can be acquired when the patient is fixating (gazing) directly towards the camera of the diagnostic device. In some cases, during the surgery the patient can be asked to gaze towards one of the two cameras that acquire the stereoscopic image-pair (e.g. with or without a special fixation light/target). In other cases, during the surgery the patient can be asked for example to gaze in between the two cameras.

In some embodiments for stereoscopic guidance overlay, the overlay is determined for the left intraoperative image and the overlay for the left intraoperative image is used as a basis for determining the overlay for the right intraoperative image (or vice versa). In these embodiments, only the overlay location for one (left or right) image is calculated (e.g. by copying the overlay location from the reference image), and the overlay for the second image is determined by shifting the overlay in the x direction (e.g., the x-direction as shown in FIG. 6A) such that the disparity between the overlay for the left image and the overlay for the right image has a disparity that corresponds to the desired depth of the overlay. This can be done for example, based on the left-right disparity, as can be calculated for image elements that are located at the same depth as the depth the overlay is meant to be perceived at. These embodiments can be used, for instance, when the patient is instructed to gaze towards one of the two cameras, such that the error due to gazing direction can be eliminated when copying the overlay from the reference image to the intraoperative image from this camera. For example, if the patient is fixating/gazing towards the left camera, the overlay can be copied from a reference image to the left intraoperative image, and the right overlay can be determined by shifting the overlay in the x direction according to a desired disparity and/or depth. This can guarantee that the overlay appears sharp and/or non-blurry, and in the same depth as the depth the overlay is meant to be perceived at.

In various embodiments, shifting the overlay in the left image is done relative to the right image in the x-direction, the y-direction, or both, and/or such that there is no rotation (or substantially no rotation) of the overlay relative to the other.

In some cases, the images (or optical channels in the case of an optical microscope) are substantially aligned but there might be a residual misalignment that isn't or cannot be digitally aligned (such as for an optical microscope). In some cases, the images are substantially without distortions but there might be residual distortions that aren't or cannot be digitally corrected (such as for an optical microscope). In some scenarios, if the images are not corrected or aligned, the shift can be along a slightly different axis, that can be determined based on a known misalignment between the two cameras (or optical channels in the case of an optical microscope) and/or known distortions of the images. In some cases, the left and right overlays can also have a slight relative rotation in the above cases. The misalignment between the two images and/or the effect of the distortion can be small enough so the two (left and right) images can appear to the brain as a clear stereoscopic image without any corrections. Nevertheless in some cases the misalignment and/or the distortions can be taken into consideration when generating a stereoscopic overlay. In these cases the shift may be not perfectly along the x direction and/or may be slightly rotated.

In some embodiments for stereoscopic guidance overlay, an overlay is copied from the coordinate system of the reference image to the coordinate system of one of the intraoperative images, and the copied overlay location is used as a basis for determining the overlay for the left and right intraoperative images. In these embodiments, the copied overlay can be shifted in the x direction to determine the overlay for each of the left and right intraoperative images (e.g., using a different shift for each of the two images). The amount of shift for each image can be such that the resulting overlay disparity corresponds to the desired depth for the overlay. The shift can also be based on the patients gazing direction. For example, when the patient is gazing towards a middle point between the two cameras, an overlay location and/or orientation can be determined with respect to either the left or right intraoperative images, and then can be shifted in the x direction by half the desired disparity leftwards and rightwards to determine the left and right overlays.

Some advantages these embodiments can include producing a visually sharp overlay at the desired depth. Additional advantages of these embodiments can include reduced computations due to using only a single copy from the reference image.

As described above, a left-right disparity of an image element appearing in the left and right images of a stereoscopic image pair can occur in systems capturing a stereoscopic image. Turning to FIGS. 6A and 6B, FIGS. 6A and 6B are left and right images (605L and 605R, correspondingly) obtained via a stereoscopic imaging device (e.g., a stereoscopic camera system comprising two cameras) showing examples of left-right disparity, according to some embodiments of the invention. FIG. 6A is an image taken from a left camera of a stereoscopic camera system (e.g., the camera corresponding to the image seen by the left eye of a user), and FIG. 6B is an image taken from the right camera of a stereoscopic camera system.

In some embodiments, two cameras in a system for capturing a stereoscopic image are intentionally misaligned in one angular degree-of-freedom (DOF) to generate a stereoscopic image, but can be aligned in two other angular DOFs. Since perfect alignment of the cameras can be impractical, residual undesired misalignment in the images generated by the misaligned cameras can be digitally corrected. For example, assume that the two (e.g., the left and the right) images in FIGS. 6A and 6B have been corrected for undesired physical misalignment between the left and right cameras. Also assume that the two images are already corrected for optical distortions generated by the cameras. In this example, the left-right disparity of identical elements in both images can be exhibited by a difference in the x coordinate of the location of the element (e.g. the location along the x axis), whereas the y coordinate can be the same.

In FIGS. 6A and 6B, two pairs of identical image elements are indicated. Image elements 610L and 610R are associated with one physical element, and image elements 620L and 620R are associated with a second physical element (e.g. a scleral blood vessel of the eye model). In the scenery that is seen in these images, the physical element 620 is closer to the cameras than physical element 610 (e.g. element 610 is deeper than element 620). The y coordinate of the location for each pair is identical, whereas the x coordinate is different. The difference, x(left)−x(right), is the left-right disparity. In the example shown in FIGS. 6A and 6B, the disparity for the scleral blood vessel 620 of the eye model is positive (D=51.3 pixels), and the disparity for image element 610 is negative (D=−20.7 pixels). The disparity can depend on a depth of the image element in the scenery. Image elements that are exactly at the designed working distance of the cameras (e.g., the distance where the FOVs of both cameras completely overlap (or substantially completely overlap)) can exhibit zero disparity, elements closer to the cameras can have positive disparity, and elements further away from the cameras can have negative disparity.

Figure 7:
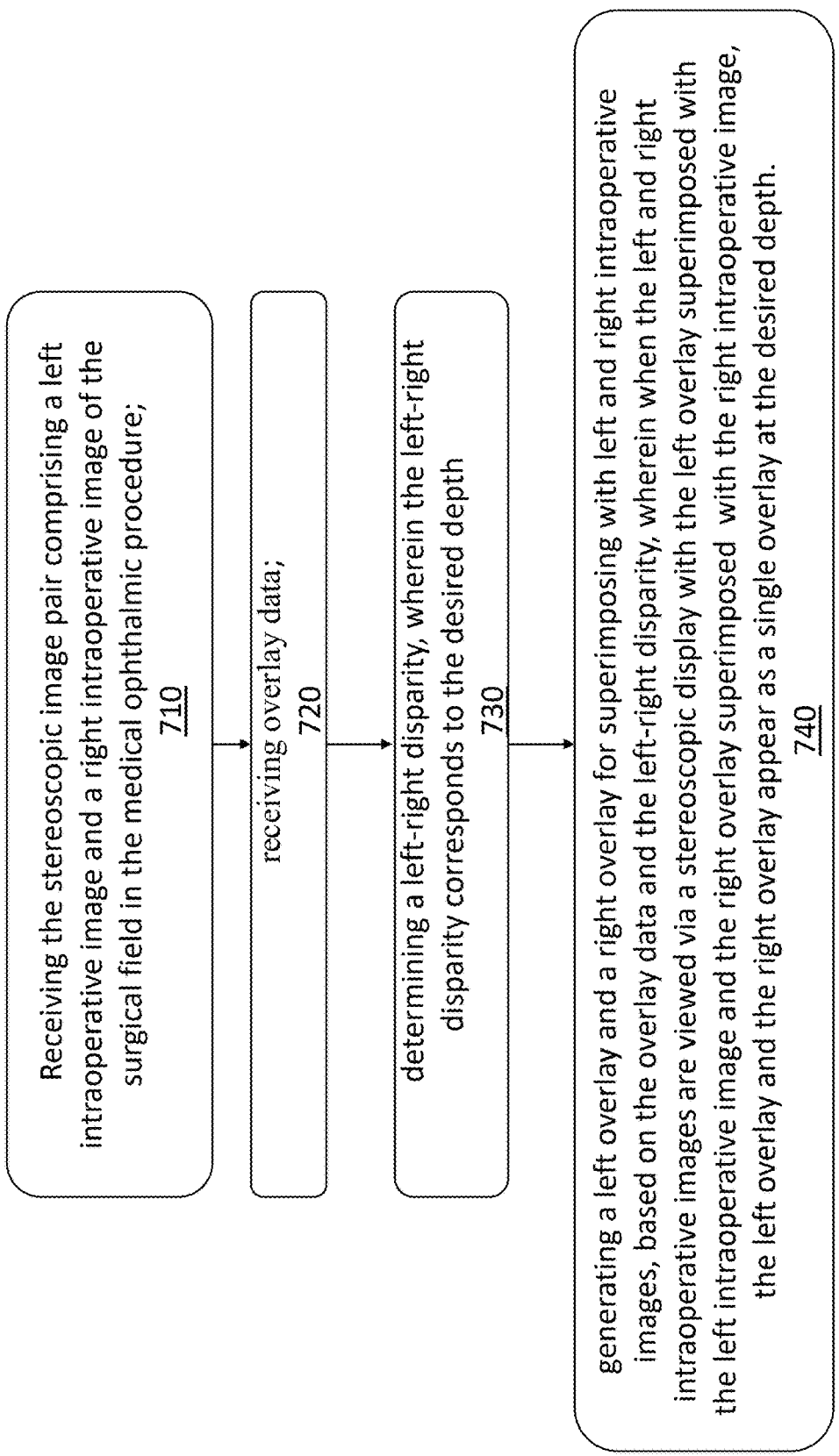
FIG. 7 is a flow chart for a method for displaying an overlay superimposed with a stereoscopic intraoperative image pair of a surgical field in a medical ophthalmic procedure, according to an illustrative embodiment of the invention.

FIG. 7 is a flow chart for a method for displaying an overlay superimposed with a stereoscopic intraoperative image pair (e.g., a left image and a right image) of a surgical field in a medical ophthalmic procedure, according to an illustrative embodiment of the invention. The method can involve receiving, by a computing device, the stereoscopic intraoperative image pair comprising a left intraoperative image and a right intraoperative image of the surgical field in the medical ophthalmic procedure (Step 710). The left intraoperative image can be a left image of a surgical field of a medical ophthalmic procedure and the right intraoperative image can be the right image of the surgical field.

The method can also involve receiving, by the computing device, overlay data (e.g., a left overlay) (Step 720). The overlay data can be overlay data as described above.

The method can also involve determining, by the computing device, a left-right disparity, wherein the left-right disparity corresponds to a desired depth (Step 730). The left-right disparity can be a number representing a distance in pixels.

In some embodiments, the left-right disparity is based on locating an element in the left intraoperative image and locating the same element in the right intraoperative image, and taking the x difference between the two. In some of these embodiments, the element can be at the desired depth of the overlay. For example, the desired depth can be the desired depth of the guidance overlay for IOL placement, and the element can be the IOL.

In some embodiments, the left-right disparity is based on locating an element from the surgical field in a left intraoperative image pair of previous stereoscopic intraoperative image pair and locating the same element in a right intraoperative image pair of previous stereoscopic intraoperative image pair, and taking the x difference between the two. In some of these embodiments, the element can be at the desired depth of the overlay, and it can be assumed that the depth of the element stays substantially the same between the time the previous frame was acquired and the time the current frame with the overlay is displayed.

In some of the embodiments where the left-right disparity is based on locating an element in the left and right images of an intraoperative image pair or of a previous stereoscopic intraoperative image pair, the element can be at a depth relative to the desired depth. The relative depth can be a known relative depth. The relative depth can be known from a typical anatomy of an eye. Alternatively, the relative depth can be known from patient-specific preoperative diagnostic measurements of the eye being operated on, from a 3D patient-specific model of the eye being operated on, and/or from an input from a user. For example, the desired depth can be the desired depth of the guidance overlay for IOL placement, the element can be the limbus of an eye, and the relative depth can be the relative depth between the limbus of the eye and the preplanned depth of the IOL.

In these embodiments, the left-right disparity can be further based on a predetermined calibration of the camera system. For instance, a depth relative to the designed working distance of the camera system can correspond to a disparity value that can be measured (e.g. during the calibration). Therefore, when a disparity value is known for an element in the surgical field (e.g. as determined from the location of the element in the left and right images), a disparity value can be determined for any depth that is relative to the depth of the element. Continuing the example above, it can be determined from the left and right images that the limbus can have a disparity of 10 pixels, and the desired depth of the IOL is 2 mm below the limbus (e.g. the preplanned depth). Based on predetermined calibration of the camera system it can be known that a relative depth of −2 mm corresponds to a disparity difference of −30 pixels. Therefore, the left-right disparity at the desired depth can be −20 pixels.

In some embodiments, a user defines the desired depth of an IOL relative to the limbus or relative to the anterior capsule (e.g., the depth of which relative to the limbus is known from a patient-specific diagnostic measurement).

In some embodiments, determining the left-right disparity is based on a distance of at least one element in the surgical field from a device (e.g., a camera-system) that captured the left and right images. For example, the distance of the element from the device can be determined by triangulation and based on a predetermined calibration of the camera system (e.g. a location in an image taken by a calibrated camera can correspond to a direction with respect to the camera, hence two directions that correspond to the two locations of the element in the left and right images can determine a distance of the element with respect to the camera system). As another example, the distance of the element from the device can be based on automatically adjusting the distance of the camera system from the element such that the element appears in focus, and based on predetermined calibration of the camera system (e.g. a focus state of the camera optics can correspond to a distance from the camera of an object that appears in focus). The at least one element can be at a depth relative to the desired depth. The relative depth can be a known relative depth. The relative depth can be known from a typical anatomy of an eye. Alternatively, the relative depth can be known from patient-specific preoperative diagnostic measurements of the eye being operated on, from a 3D patient-specific model of the eye being operated on, and/or from an input from a user.

In some embodiments, misalignments and optical distortions of the cameras in the camera system are taken into consideration when determining the left-right disparity.

In some embodiments, optical distortion of the cornea can be compensated for when determining the left-right disparity. The optical distortion of the cornea can be known from a typical anatomy of an eye, patient-specific preoperative diagnostic measurements of the eye being operated on, a 3D patient-specific model of the eye being operated on, and/or an input from a user. For example, a correspondence between relative depth and disparity difference for the camera system can be calibrated without the presence of an eye and without optical elements having an optical power (e.g. representing a cornea), and the effect of the optical power of the cornea can be taken into consideration when determining the left-right disparity. For instance, a relative depth of −2 mm can correspond to an effective relative depth that is different that −2 mm, such as −1.4 mm, due to the optical power of the cornea. As another example, a correspondence between relative depth and disparity difference for the camera system can be calibrated with an optical element representing a typical cornea (e.g. having an optical power equivalent to that of a typical cornea).

In some embodiments, the left right disparity is based on selecting a region in the left intraoperative image and a region in the right intraoperative region. The regions can be selected to have at least a partial overlapping or a common element such that a cross-correlation of the selected left and right regions results in a disparity value.

The method can also involve generating, by the computing device, a left overlay and a right overlay for superimposing with the left and right intraoperative images, based on the overlay data and the left-right disparity (Step 740), wherein when the left and right intraoperative images are displayed via a stereoscopic display with the left overlay superimposed with the left intraoperative image and the right overlay superimposed with the right intraoperative image, the left overlay and the right overlay appear as a single overlay at the desired depth. For example, the single overlay can appear as one three-dimensional element to a user.

The stereoscopic display can be for example a 3D monitor with or without glasses (e.g. active shutter glasses or polarized glasses), a 3D head mounted display (HMD), or a binocular surgical microscope.

In some embodiments, for an overlay for IOL placement, the disparity can be determined by detecting the IOL in both images (e.g., the left and right intraoperative images), such that the overlay can be perceived by a user as appearing at the same depth as the IOL. In some embodiments, detecting the IOL can be performed by various image processing algorithms as are known in the art. In some embodiments, it is not required that the entire IOL is detected or that the IOL axis marks are detected in order to detection the IOL in each of the images. In some embodiments, at least one element of the IOL is detected in the left and right images and used as the basis for the left-right disparity at the IOL depth. The one element can be an axis mark, an IOL edge point, or an IOL haptic edge point. In some embodiments, the IOL model (e.g., shape, contour and/or axis marks appearance) is known and the IOL model can be used to identify one or more elements for the left-right disparity determination. In some embodiments, the IOL type or model is unknown, and the detection method may be generic and work for all types of IOLs. For example, one method may be based on detecting an edge along outgoing rays starting from the approximated location of the pupil center (e.g. as copied from the preoperative reference image). In some embodiments, detecting the IOL can be performed by a deep learning network that is trained to identify various types of IOLs. In some embodiments, for an overlay for IOL placement, the disparity can be determined without detecting the IOL. For instance, the disparity can be determined before the IOL is inserted to the patient's eye. In these embodiments, a disparity can be calculated for an element that has a known relative depth relative to the IOL desired depth, and the left-right disparity can be determined based on this disparity and the known relative depth.

In some embodiments, the left-right disparity can be determined for a transparent anatomy. In these embodiments, image elements at a desired depth can be difficult to locate as due to the transparent nature of the anatomy. For example, a stereoscopic overlay for guiding a capsulotomy can be meant to be perceived by a surgeon to be at the depth of an anterior capsule, and a stereoscopic overlay for guiding an LRI procedure can be meant to be perceived by the surgeon to be at the depth of a desired LRI location on the cornea. Image elements in the anterior capsule and cornea of an eye may not be detected since both are transparent. In these embodiments, a disparity can be determined for an element that can be detected in the image-pair, and that has a known relative depth relative to the transparent anatomical element, and the left-right disparity can be determined based on this disparity and the known relative depth. In these embodiments, the disparity can be determined based on a patient-specific 3D model of the eye, for example a 3D model generated by a preoperative diagnostic device (e.g., a Pentacam® by Oculus, as is known in the art). As another example, the 3D model can be generated by an intraoperative OCT (e.g. an alignment between the iOCT and the camera can be known, as described previously). The 3D model can be used to determine a depth of a desired anatomical element that is transparent in the image (e.g., the anterior capsule) relative to a depth of an anatomical element that is not transparent in the image, such as elements of the limbus.

In some embodiments, the 3D model is registered to a camera system coordinate system. e.g. based on copying locations from a preoperative image, taken simultaneously with sampling the data that was used to build the 3D model, to the intraoperative image.

In some embodiments, the optical power of the cornea may be taken into consideration when using the 3D model to determine the desired left-right disparity of image elements that are meant to be perceived as being below the cornea. The optical power can be determined from diagnostic measurements and/or can be derived from the known 3D model of the cornea.

In some embodiments, the left-right disparity at the desired depth can be determined based on a non-patient specific 3D eye model. The non-patient specific model can be scaled and/or modified to fit the actual white-to-white distance of the eye of the patient and/or an actual axial length of the patient's eye, as known, for example, from diagnostic tests. In these embodiments, a disparity can be determined for an element that can be detected in the image-pair, and that has a known relative depth relative to the desired depth, and the left-right disparity can be determined based on this disparity and the known relative depth. The known relative depth can be known from the non-patient specific 3D eye model or from the scaled and/or modified non-patient specific 3D eye model.

In some embodiments, the left-right disparity at the desired depth can be determined based on the left-right disparity of a tooltip located at the desired depth, and/or of elements near the tooltip. For example, an anterior capsule can be transparent such that until a surgeon begins to perform a capsulotomy, the anterior capsule cannot be seen. When the tool begins generating the capsulotomy, the tool can be detected and image elements near the tip of the tool can be used to determine a left-right disparity based on the left and right images. The image elements can include for instance the tooltip and/or the capsule tissue.

In some embodiments, a depth of the overlay may be controlled by the surgeon. Changing the depth may be continuous or discrete. For example, a supervising surgeon may control the depth of a cursor (e.g. a stereoscopic cursor) that is overlaid on the intraoperative image and is controlled by the surgeon, e.g. by manipulating a wireless mouse or by head gestures. The cursor can be used to guide a resident surgeon. In some embodiments, the user may switch between several discrete overlay depths. This feature can be relevant in ophthalmic surgery, where transparent tissues allow the surgeon to simultaneously focus on tissues of varying depths, such as the cornea, iris, capsule and/or lens (e.g., when a depth of field, or the depth of focus, of the camera or microscope is high enough). In some embodiments, the left-right disparity for each depth is automatically determined based on using a patient specific or a non-patient specific 3D eye model. In some embodiments, the left-right disparity for each depth is automatically determined based on using an intraoperative OCT. In some embodiments, the left-right disparity for each depth is based on calculating the left-right disparity of various image elements and generating a real-time 3D map from the stereoscopic image.

In some embodiments, the left-right disparity can be determined based on a region in the left intraoperative image and a region in the right intraoperative image (e.g., two regions having the same size and location). The left-right disparity can be determined based on cross-correlation of the left and right regions. The cross-correlation can find an x-shift that gives a highest correlation score between the left and right regions. The x-shift that corresponds to the highest correlation score can be determined as the disparity of the region. In cases where the residual misalignment and/or optical distortions are not corrected, similar methods can be used to find a shift along a slightly different axis and/or allowing small rotations between the regions. In some cases, correlation can be performed in the Fourier domain. In some cases, when image elements in the region are associated with physical elements in the surgical field having different depths, the cross-correlation can determine the disparity of the most dominant element.

During IOL placement, it can be desirable for a surgeon to verify that an IOL is positioned at a correct depth. It can also be desirable for a surgeon to verify that an IOL is positioned without any tilt. In some embodiments, an overlay can be generated and superimposed with the intraoperative image such that it appears at the correct depth (e.g., a desired depth) and tilt (e.g., without tilt) for the IOL insertion. The surgeon can align the IOL with the overlay, for example, tilt and/or move the IOL to ensure proper placement of the IOL.

In some embodiments, the overlay for verifying proper placement for an IOL (e.g. for verifying proper depth and/or tilt) is a stereoscopic overlay. For example, the overlay can be a guidance overlay for guiding a surgeon during IOL placement, allowing the surgeon to verify that the IOL is positioned at the pre-planned depth and without any undesired tilt. In some embodiments, a circle serves as such a guidance overlay. The circle can be superimposed on each of the images of the stereoscopic image-pair such that the circle appears in the desired depth (e.g. within the capsular bag), and the surgeon aligns the rim of the IOL with the circle. The position of the circle in the two channels can be determined based on a disparity using the previously described method. The circle can be displayed such that it is centered on the visual axis of the eye (e.g. as copied from a reference image). Alternatively, the circle can be displayed such that it is centered on the actual IOL location (e.g. as detected in the image).

In some embodiments, a 3D overlay can be generated, for example, a cage or an object that has an outline similar to an IOL and positioned at a depth within the intraoperative stereoscopic image that is the correct depth (e.g., a desired depth) for the IOL insertion, and with the correct tilt (e.g. without tilt). The surgeon can align the IOL with the 3D overlay object, for example, tilt and/or move the IOL in three dimensions to ensure proper placement of the IOL. In various embodiments, the desired depth is received and/or derived from patient specific information.

In some embodiments, a multi-depth stereoscopic overlay is determined. The multi-depth stereoscopic overlay can be determined by determining multiple single depth overlays and optionally connecting them together (e.g., by lines). In some embodiments, a multi-depth stereoscopic overlay is determined by determining multiple single depth overlay points, and connecting them together. The location of the single depth overlays and/or points in the left and right intraoperative images can be determined based on a disparity using the previously described method, and once their location is determined they can be connected in each of the images. In some embodiments, a 3D model of a 3D overlay is rendered from two points of views of the cameras. In these embodiments, if the overlay is to appear below the cornea, the optical power of the cornea can be compensated for.

As an example, for a multi-depth stereoscopic overlay, a wireframe cage can serve as a guidance overlay for verifying proper placement for an IOL (e.g., for verifying proper depth and/or tilt). The shape of the cage can be determined so it envelopes the body of the IOL (e.g. without the IOL haptics, e.g. when the IOL model is known). For example, the wireframe cage can include multiple single-depth circles having varying diameters, each circle having a different depth and all circles centered along a single axis. Each of the circles can be copied to the left and right intraoperative images such that it appears at its corresponding depth. The location of each circle in each of the left and right intraoperative images can be determined based on a disparity using the previously described method. Optionally, the circles can be connected (e.g. by lines every 30 degrees).

In another example for a multi-depth stereoscopic overlay, the overlay may be an oblique line (e.g. a line starting at an entry point to the eye and going deeper into the eye). Such an overlay may serve as a teaching guidance for a desired trajectory of a tool inserted into the eye, for instance toward the center of the anterior capsule. The line can be represented as two points (e.g., the two edges of the line). For example, these two points can be marked by a supervising surgeon on a snapshot of the intraoperative image of one of the two stereoscopic channels. Each of these points can be copied to the other channel with a single disparity. For instance, the entry point can be copied using the same disparity as the limbus, and the target point can be copied using a disparity that corresponds to the depth of the center of the anterior capsule (e.g., as determined based on a patient-specific 3D model of the eye, and with compensation for the optical power of the cornea). Then, the two points can be connected in the coordinate system of the second channel to re-construct the line. The final stereoscopic overlay can appear as an oblique line penetrating the eye.

In some embodiments, the actual IOL depth and/or tilt can be automatically determined. For example, once an IOL is positioned in the capsular bag, its depth and/or tilt can be determined on-demand or continuously. For example, in a system that has an integrated intraoperative OCT, an anterior segment volumetric scan can reveal an actual depth and tilt of the IOL. As another example, the disparity of different points in the IOL, such as along the perimeter of the IOL body, can be determined. The IOL depth/tilt can be determined based on i) the disparity values, ii) a known shape (e.g., 3D model) of the IOL, iii) a known camera system calibration (e.g., predetermined), and/or iv) a known optical power of the cornea (e.g., measured preoperatively by a diagnostic device). If the disparity is not equal for all points along the perimeter of the IOL body, it can indicate that the IOL is tilted.

In some embodiments, the determination is based on an iOCT. In some embodiments, the determination is based on disparity of the IOL and/or disparity of elements in the IOL. In some embodiments, the determined actual IOL depth and/or tilt is conveyed to the surgeon (e.g. as numbers, as a symbol, as a schematic side view of an eye with an IOL symbol, etc.).

Figure 8:
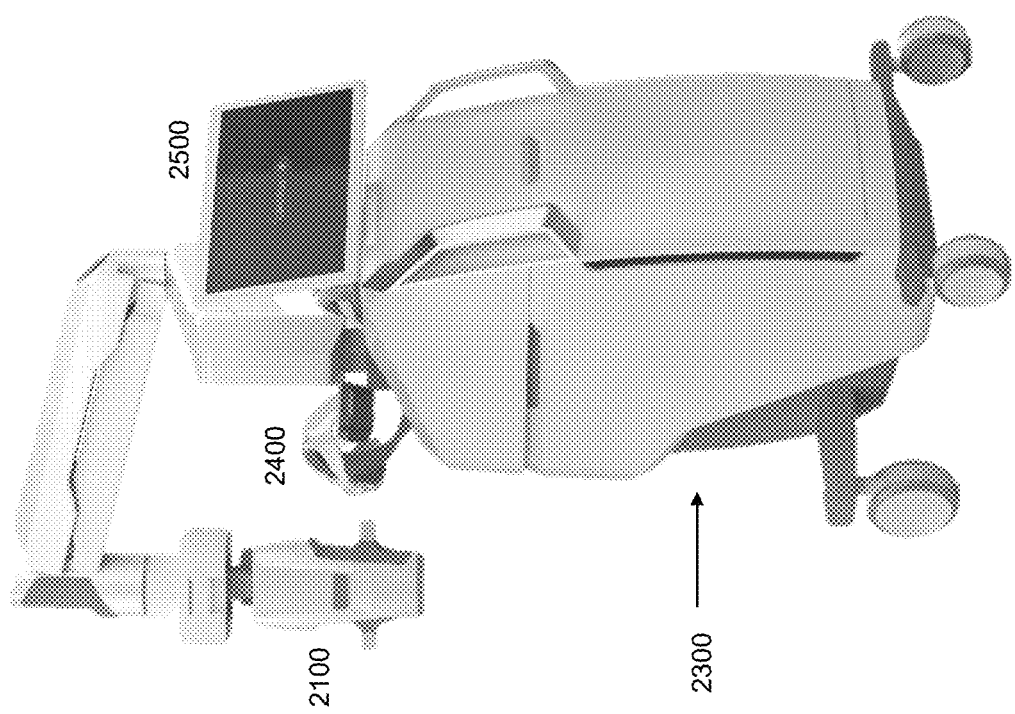
FIG. 8 is a diagram of an example of a system for overlaying guidance information, according to some embodiments of the invention.
Figure 8:
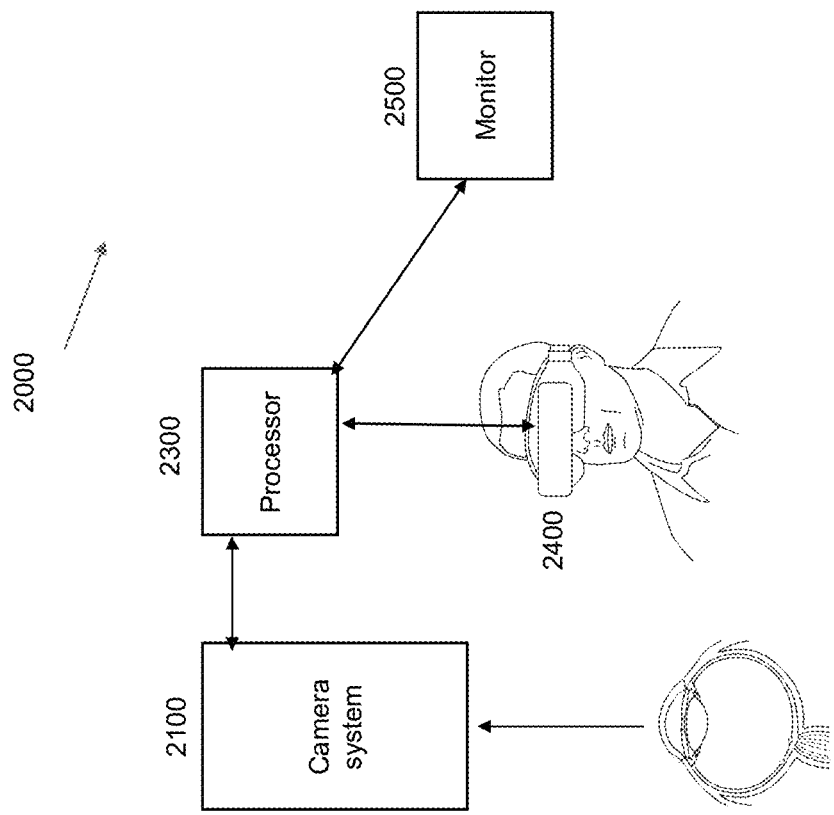

FIG. 8 is a diagram of an example of a system 2000 for overlaying guidance information, according to some embodiments of the invention. The system can include a camera system 2100 (e.g. a stereoscopic camera system), a processor 2300 (e.g. a PC), a head wearable display (HWD) 2400, and a monitor 2500.

During operation, the processor 2300 can receive and read images from cameras in the camera system 2100, process the images, and stream the processed images to the HWD 2400 and/or the monitor 2500. The processing of the images can involve standard image processing (e.g. de-Bayer, automatic gain control, distortion correction), adding images in PIP view or in side-by-side view, and/or overlaying guidance information, e.g. as guidance symbols. In some embodiments, the monitor 2500 is a 3D monitor. The 3D monitor can be viewed with special glasses to see a 3D image. The processor can include a video processing unit.

In some embodiments, an intraoperative image is displayed such that it is rotated by 180 degrees. For example, during a posterior segment ophthalmic surgery, when using a non-contact wide-angle viewing system, the intraoperative image can be rotated to, for example, compensate for the inverting effect of the non-contact lens. In another example, rotating an intraoperative image by 180 degrees can allow a brain surgeon to move from one side of the surgical table to the other without having to rotate the stereoscopic camera system accordingly. Rotating the intraoperative image by 180 degrees can involve switching both the left and right images. For example, displaying the video from the left camera to the right eye, and vice versa. In these embodiments, the processor 2300 can receive and read the pixels from the cameras in the camera system 2100 in an opposite order, e.g., the last pixel in the last row of the sensor is read first, and the first pixel of the first row of the sensor is read last.

In some embodiments, the system 2000 includes up to three HWDs 2400 that can simultaneously display a live image. The images displayed via the three HWDs can be the same or different. For example, a supervising surgeon may zoom out, freeze the image and/or use menus for drawing markings on the image, while at the same time the resident is viewing the live image without any change. In some embodiments, the images have varying magnifications, e.g. when the magnification is digital.

In some embodiments, the camera system 2100 is assembled on a standard surgical microscope (not shown). In some embodiments, the camera system 2100 replaces the microscope oculars. In some embodiments, the system 2000 includes both the camera system 2100 and microscope oculars. In these embodiments, beam-splitters can be used to partially deflect the optical images towards the cameras. In some embodiments, the camera system 2100 has a single camera. In some embodiments, the camera system has a stereoscopic camera (e.g. two cameras).

In some embodiments, when the camera system 2100 is assembled on a standard surgical microscope, in addition to or instead of overlaying the guidance information on an image displayed via an HWD and/or a monitor, the guidance information may be superimposed on the optical image viewed through the oculars (e.g., beam-splitters may be used to deflect the overlay images towards the oculars). In these embodiments, the overlay images can include the guidance information on a black background, such that only the guidance information is superimposed on the optical image generated by the surgical microscope, and other areas in the overlay images do not obscure the optical image. The overlay images in these embodiments can require a correction for allowing the overlay to be accurately superimposed on the optical image viewed via the oculars. The correction can be based on a predetermined alignment between the camera and the corresponding optical image as viewed via the ocular (e.g. that takes into consideration also the different optical distortions of the two channels).

Figure 9:
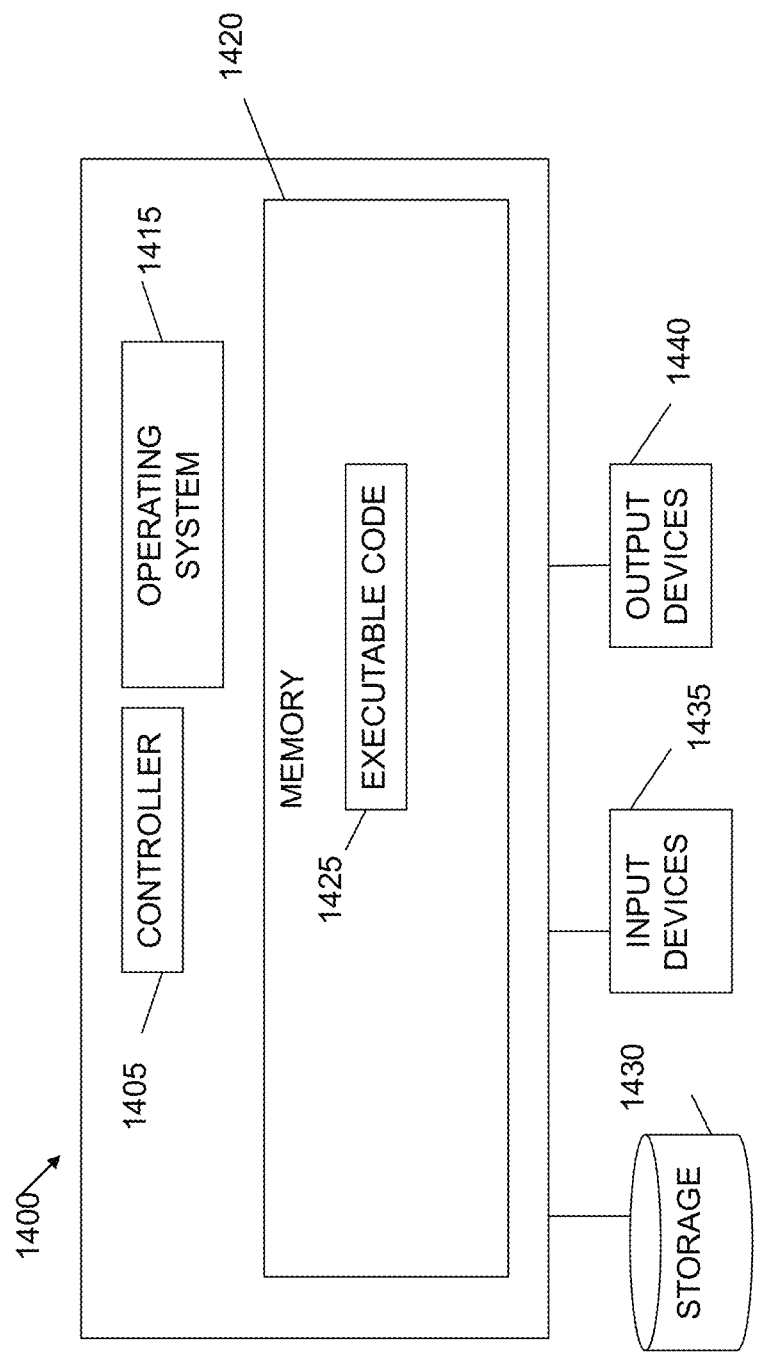
FIG. 9 shows a block diagram of a computing device which can be used with embodiments of the invention.

FIG. 9 shows a block diagram of a computing device 1400 which can be used with embodiments of the invention. Computing device 1400 can include a controller or processor 1405 that can be or include, for example, one or more central processing unit processor(s) (CPU), one or more Graphics Processing Unit(s) (GPU or GPGPU), FPGAs, ASICs, combination of processors, video processing units, a chip or any suitable computing or computational device, an operating system 1415, a memory 1420, a storage 1430, input devices 1435 and output devices 1440. The computing device 1400 can be the computer/processor as described above.

Operating system 1415 can be or can include any code segment designed and/or configured to perform tasks involving coordination, scheduling, arbitration, supervising, controlling or otherwise managing operation of computing device 1400, for example, scheduling execution of programs. Memory 1420 can be or can include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 1420 can be or can include a plurality of, possibly different memory units. Memory 1420 can store for example, instructions to carry out a method (e.g. code 1425), and/or data such as user responses, interruptions, etc.

Executable code 1425 can be any executable code, e.g., an application, a program, a process, task or script. Executable code 1425 can be executed by controller 1405 possibly under control of operating system 1415. For example, executable code 1425 can when executed cause masking of personally identifiable information (PII), according to embodiments of the invention. In some embodiments, more than one computing device 1400 or components of device 1400 can be used for multiple functions described herein. For the various modules and functions described herein, one or more computing devices 1400 or components of computing device 1400 can be used. Devices that include components similar or different to those included in computing device 1400 can be used, and can be connected to a network and used as a system. One or more processor(s) 1405 can be configured to carry out embodiments of the invention by for example executing software or code. Storage 1430 can be or can include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, NN model data, parameters, etc. can be stored in a storage 1430 and can be loaded from storage 1430 into a memory 1420 where it can be processed by controller 1405. In some embodiments, some of the components shown in FIG. 10 can be omitted.

Input devices 1435 can be or can include for example a mouse, a keyboard, a touch screen or pad or any suitable input device. It will be recognized that any suitable number of input devices can be operatively connected to computing device 1400 as shown by block 1435. Output devices 1440 can include one or more displays, speakers and/or any other suitable output devices. It will be recognized that any suitable number of output devices can be operatively connected to computing device 1400 as shown by block 1440. Any applicable input/output (I/O) devices can be connected to computing device 1400, for example, a wired or wireless network interface card (NIC), a modem, printer or facsimile machine, a universal serial bus (USB) device or external hard drive can be included in input devices 1435 and/or output devices 1440.

Embodiments of the invention can include one or more article(s) (e.g. memory 1420 or storage 1430) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carny out methods disclosed herein.

One skilled in the art will realize the invention can be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

Although embodiments of the invention are not limited in this regard, discussions utilizing terms such as, for example. "processing", "computing", "calculating", "determining". "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

The invention claimed is:

1. A method for displaying an overlay superimposed with an intraoperative image of a surgical field in a medical ophthalmic procedure, the method comprising:

receiving, by a computing device, the overlay for superimposing with the intraoperative image that is in real-time;

receiving, by a computing device, the intraoperative image of the surgical field in the medical ophthalmic procedure, the surgical field including an element that is to appear as above the overlay, said element comprising at least one of: a tool, an iris, a sclera, a corneal reflection, an air bubble, a part of a hand, and a lens fragment, wherein at least one portion of the intraoperative image is associated with the element; and displaying, by the computing device, the overlay superimposed with the intraoperative image such that an appearance of the overlay in the at least one portion is different than the appearance of the overlay outside of the at least one portion and the overlay appears as below the element and occluded by the element.

2. The method of claim 1, wherein the overlay is determined based on a preoperative image of an eye, a preoperative OCT, the intraoperative image, a previous intraoperative image, an intraoperative OCT, data from a diagnostic device, data from a phaco-vitrectomy system, a user input, or any combination thereof.

3. The method of claim 1, wherein the overlay comprises: a guidance overlay for an intraocular lens (IOL) placement, a guidance overlay for a capsulotomy, a guidance overlay for an incision, an enhancement of a membrane or part of a membrane, an enhancement of a capsule or part of a capsule, symbolic overlay, textual overlay, pictorial overlay, or any combination thereof.

4. The method of claim 1, wherein the overlay is superimposed such that inside of the at least one portion the overlay is not superimposed and outside of the at least one portion the overlay is superimposed.

5. The method of claim 1, wherein the displayed overlay appearances in the at least one portion versus outside of the at least one portion differ by at least one of: the overlay transparency, the overlay brightness, the overlay pattern, and the overlay color.

6. The method of claim 1, further comprising classifying, by the computing device, a pixel of the intraoperative image as being in the at least one portion based on one of the intraoperative image, a previous intraoperative image, or any combination thereof.

7. The method of claim 6, wherein at least one of the intraoperative image and the previous intraoperative image is segmented, and wherein the classification of a pixel of the intraoperative image as being in the at least one portion is based on the segmentation.

8. The method of claim 7, further comprising classifying the segments as one of a: pupil, iris, sclera, tool, corneal reflection, air bubble, part of a hand, lens fragment, IOL, or IOL reflections, and determining whether the classified segments should occlude the overlay, based on a type of overlay and predefined rules.

9. The method of claim 6, wherein the intraoperative image is one of an intraoperative stereoscopic image pair and the classifying of the pixel is based on the pixel disparity calculated from the stereoscopic image pair.

10. The method of claim 6, wherein the classification is based on a gray level value or color value of at least one of the pixels of the intraoperative image, a neighboring pixel, or any combination thereof.

11. The method of claim 1, further comprising classifying, by the computing device, a pixel of the intraoperative image as being in the at least one portion based on an intraoperative OCT.

12. The method of claim 11, wherein data generated by the intraoperative OCT are associated with the pixel of the intraoperative image based on alignment between the intraoperative OCT and a camera that generated the intraoperative image.

13. The method of claim 1, wherein the element is a tool and further comprising, classifying by the computing device, a pixel as being in the at least one portion based at least on a tool tracker.

14. The method of claim 13, wherein the classifying is based on a relative position and orientation between the tool and the camera that generated the intraoperative image.

* * * * *